(12) United States Patent
Alcorn et al.

(10) Patent No.: US 12,390,808 B2
(45) Date of Patent: Aug. 19, 2025

(54) DEVICE AND METHOD FOR DETECTING NUCLEIC ACIDS IN BIOLOGICAL SAMPLES

(71) Applicant: Definitive Biotechnologies LLC, Elkridge, MD (US)

(72) Inventors: Timothy Alcorn, Raleigh, NC (US); Steven Dietl, Raleigh, NY (US); Robert Altavela, Webster, NY (US); Michael Carlotta, Lilburn, GA (US); John C. Detter, Melbourne Beach, FL (US); Todd Haran, Bloomfield, NY (US); Michael Murray, Bloomfield, NY (US); Scott Rosebrough, Avon, NY (US); Jeffrey Serbicki, Holley, NY (US)

(73) Assignee: DEFINITIVE BIOTECHNOLOGIES LLC, Elkridge, MD (US)

( * ) Notice: Subject to any disclaimer, the term of this patent is extended or adjusted under 35 U.S.C. 154(b) by 748 days.

(21) Appl. No.: 17/647,828

(22) Filed: Jan. 12, 2022

(65) Prior Publication Data

US 2022/0219169 A1 Jul. 14, 2022

Related U.S. Application Data

(60) Provisional application No. 63/243,005, filed on Sep. 10, 2021, provisional application No. 63/154,217, (Continued)

(51) Int. Cl.
*B01L 3/00* (2006.01)
*B01F 33/302* (2022.01)
(Continued)

(52) U.S. Cl.
CPC ... *B01L 3/502715* (2013.01); *B01L 3/502723* (2013.01); *B01L 3/50273* (2013.01); (Continued)

(58) Field of Classification Search
CPC ......... B01L 3/502715; B01L 3/502723; B01L 3/50273; B01L 3/502738; B01L 7/00;
(Continued)

(56) References Cited

U.S. PATENT DOCUMENTS 6,465,639 B1 10/2002 van Gemen et al.
7,217,542 B2 5/2007 Tyvoll et al.
(Continued)

FOREIGN PATENT DOCUMENTS

EP 0305399 A1 3/1989
EP 0389063 A2 9/1990
(Continued)

OTHER PUBLICATIONS

International Search Report and Written Opinion for Application No. PCT/US2022/012178, dated Apr. 1, 2022, 21 pages.
(Continued)

*Primary Examiner* — Jennifer Wecker
*Assistant Examiner* — Oyeleye Alexander Alabi
(74) *Attorney, Agent, or Firm* — McCarter & English, LLP

(57) ABSTRACT

A device for amplifying and detecting nucleic acids in a biological sample has a sample port for receiving a biological sample, a solid-state membrane, a sample conduit, a lysis station, a wash station, an elution station, a waste chamber, and a reaction chamber. The sample port, lysis station and sample conduit are configured to mix a sample and lysis agent to form a sample-lysis mixture, pass the mixture across the solid-state membrane to capture nucleic acids in the sample therein, and receive the remainder of the mixture in the waste chamber. The wash station directs a wash solution across the solid-state membrane and into the waste chamber to purify nucleic acids captured in the membrane. The elution station directs an eluent across the membrane,
(Continued)

elutes captured nucleic acids from the membrane, and passes the captured nucleic acids into the reaction chamber for amplifying and detecting the captured nucleic acids.

36 Claims, 18 Drawing Sheets

Related U.S. Application Data filed on Feb. 26, 2021, provisional application No. 63/136,435, filed on Jan. 12, 2021.

(51) Int. Cl.

| | |
|---|---|
| *B01F 33/3033* | (2022.01) |
| *B01L 7/00* | (2006.01) |
| *B01L 9/00* | (2006.01) |
| *B65G 47/80* | (2006.01) |
| *B82Y 20/00* | (2011.01) |
| *B82Y 30/00* | (2011.01) |
| *B82Y 40/00* | (2011.01) |
| *C12M 1/34* | (2006.01) |
| *C12M 3/06* | (2006.01) |
| *C12N 1/14* | (2006.01) |
| *C12N 1/20* | (2006.01) |
| *C12Q 1/02* | (2006.01) |
| *C12Q 1/6806* | (2018.01) |
| *C12Q 1/6844* | (2018.01) |
| *C12Q 1/6848* | (2018.01) |
| *C12Q 1/686* | (2018.01) |
| *G01N 15/10* | (2024.01) |
| *G01N 15/14* | (2024.01) |
| *G01N 15/1433* | (2024.01) |
| *G01N 21/29* | (2006.01) |
| *G01N 21/65* | (2006.01) |
| *G01N 33/543* | (2006.01) |
| *G01N 33/574* | (2006.01) |
| *G01N 33/58* | (2006.01) |

(52) U.S. Cl.
CPC .......... *B01L 3/502738* (2013.01); *B01L 7/00* (2013.01); *C12Q 1/6806* (2013.01); *B01L 2200/04* (2013.01); *B01L 2200/0684* (2013.01); *B01L 2400/06* (2013.01); *C12Q 1/6844* (2013.01)

(58) Field of Classification Search
CPC ......... B01L 2200/04; B01L 2200/0684; B01L 2400/06; B01L 2200/10; B01L 2200/16; B01L 2300/044; B01L 2300/0672; B01L 2400/0478; B01L 2400/0481; B01L 3/502761; B01L 7/52; C12Q 1/6806; C12Q 1/6844; G01N 35/00029; G01N 2035/00148; G01N 2035/00158; G01N 2035/00346
See application file for complete search history.

(56) References Cited

U.S. PATENT DOCUMENTS

| | | | |
|---|---|---|---|
| 7,374,913 B2 | 5/2008 | Nagamine | |
| 7,846,695 B2 | 12/2010 | Nagamine | |
| 7,851,186 B2 | 12/2010 | Nagamine | |
| 7,893,251 B2 | 2/2011 | Lorenz | |
| 8,017,357 B2 | 9/2011 | Notomi et al. | |
| 8,420,015 B2 | 4/2013 | Ganesan et al. | |
| 8,691,592 B2 | 4/2014 | Chen et al. | |
| 8,911,938 B2 | 12/2014 | Mauk et al. | |
| 9,132,398 B2 | 9/2015 | Zhou et al. | |
| 9,409,166 B2 | 8/2016 | Mauk et al. | |
| 9,476,102 B2 | 10/2016 | Bau et al. | |
| 9,617,532 B2 | 4/2017 | Fabis et al. | |
| 9,752,182 B2 | 9/2017 | Collier et al. | |
| 9,822,356 B2 | 11/2017 | Ismagilov et al. | |
| 9,909,168 B2 | 3/2018 | Notomi et al. | |
| 9,976,176 B2 | 5/2018 | Bau et al. | |
| 10,407,676 B2 | 9/2019 | Poehmerer et al. | |
| 10,538,804 B2 | 1/2020 | Tan et al. | |
| 10,596,566 B2 * | 3/2020 | Mauk ........................ B01L 7/52 |
| 10,774,368 B2 | 9/2020 | Gaeta | |
| 10,808,276 B2 | 10/2020 | Voss | |
| 10,844,369 B2 | 11/2020 | Quan | |
| 11,162,936 B2 | 11/2021 | Holmes et al. | |
| 11,199,489 B2 | 12/2021 | Gibbons et al. | |
| 2003/0152974 A1 * | 8/2003 | Gauch ................ C12N 15/1017 |
| | | | 536/25.4 |
| 2007/0128646 A1 | 6/2007 | Fiandaca et al. | |
| 2007/0221563 A1 | 9/2007 | Sakaino et al. | |
| 2012/0178091 A1 * | 7/2012 | Glezer .................. B01L 3/5027 |
| | | | 435/6.12 |
| 2013/0309679 A1 | 11/2013 | Ismagilov et al. | |
| 2016/0263577 A1 * | 9/2016 | Ismagilov ............... B01L 3/523 |
| 2017/0096702 A1 | 4/2017 | Bau et al. | |
| 2017/0274381 A1 * | 9/2017 | Selden ................. C12Q 1/6806 |
| 2018/0236446 A1 | 8/2018 | Malkin et al. | |
| 2020/0362399 A1 | 11/2020 | Cheng et al. | |
| 2021/0039094 A1 | 2/2021 | Mauk et al. | |
| 2022/0016623 A1 | 1/2022 | Nobile et al. | |
| 2022/0098575 A1 | 3/2022 | Van Den Boom et al. | |
| 2022/0326125 A1 | 10/2022 | Ueda et al. | |
| 2023/0078644 A1 | 3/2023 | Alcorn et al. | |

FOREIGN PATENT DOCUMENTS

| | | |
|---|---|---|
| JP | H06-165676 A | 6/1994 |
| WO | 224902 A1 | 9/2000 |
| WO | 2016/065300 A1 | 4/2016 |
| WO | 2016/161402 A1 | 10/2016 |
| WO | 2022/024935 A1 | 2/2022 |

OTHER PUBLICATIONS

Kim et al., A rapid and economic in-house DNA purification method using glass syringe filters. PLoS One. Nov. 18, 2009;4(11):8 pages.

Pud et al., Mechanical Trapping of DNA in a Double-Nanopore System. Nano Lett. Dec. 14, 2016;16(12):8021-8028.

Tisch Scientific, Tisch Scientific Glass Fiber Syringe Filters, 2.7 um, 13 mm, Nonsterile, 100 Pack, SF18317. 1 page. Accessed online Feb. 21, 2023.

Varongchayakul et al., A Solid-State Hard Microfluidic-Nanopore Biosensor with Multilayer Fluidics and On-Chip Bioassay/ Purification Chamber. Adv Funct Mater. Dec. 12, 2018;28(50):1804182, 9 pages.

\* cited by examiner

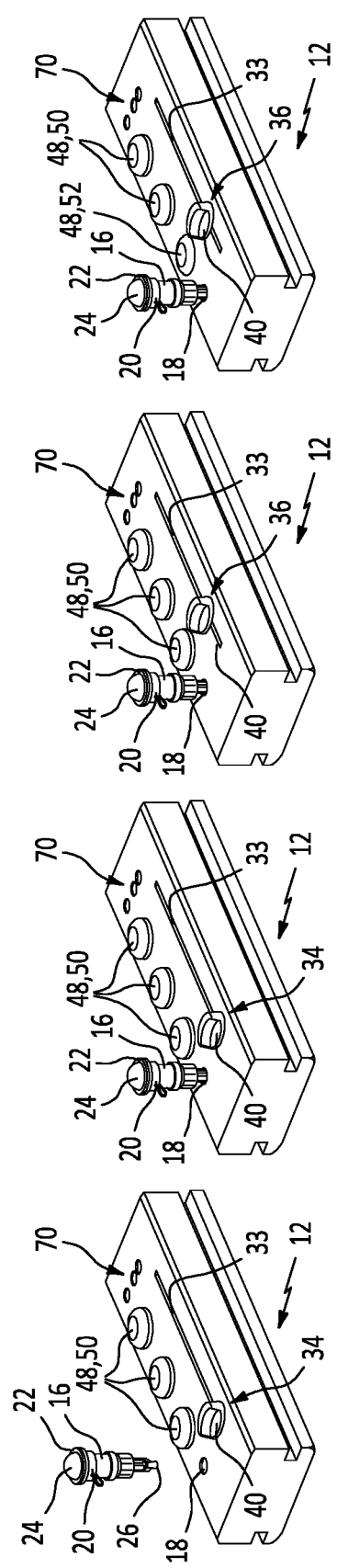
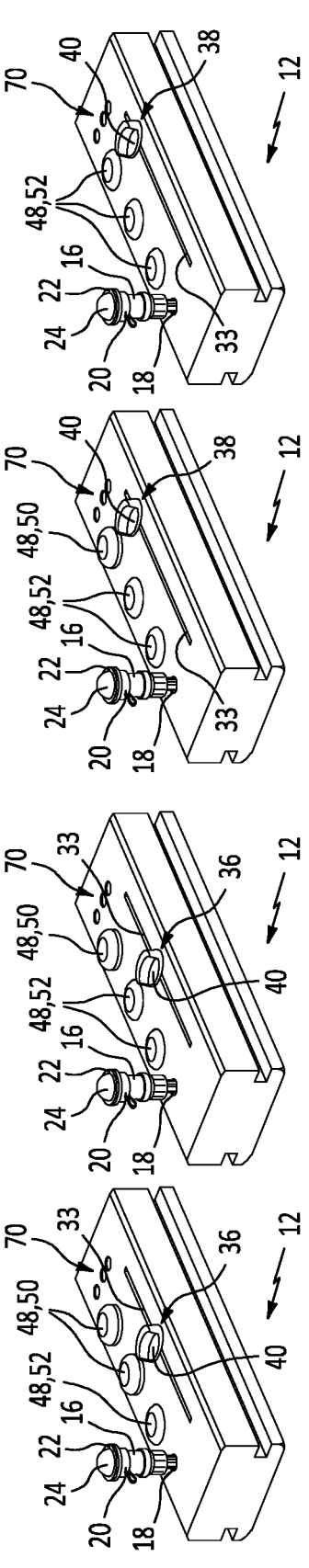
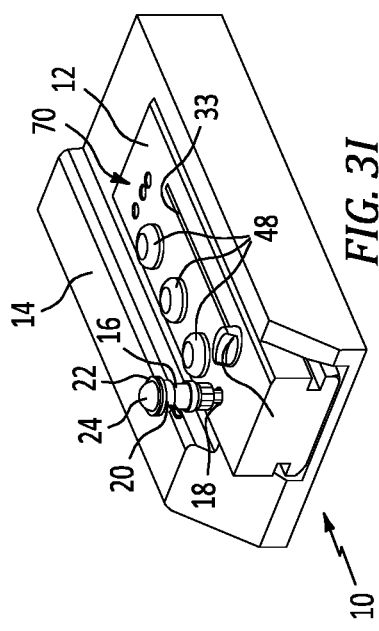

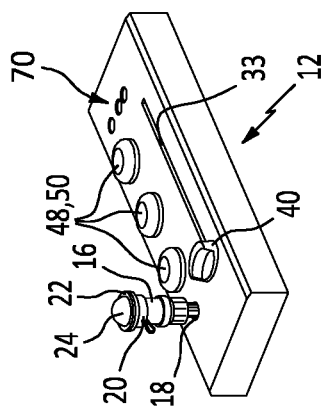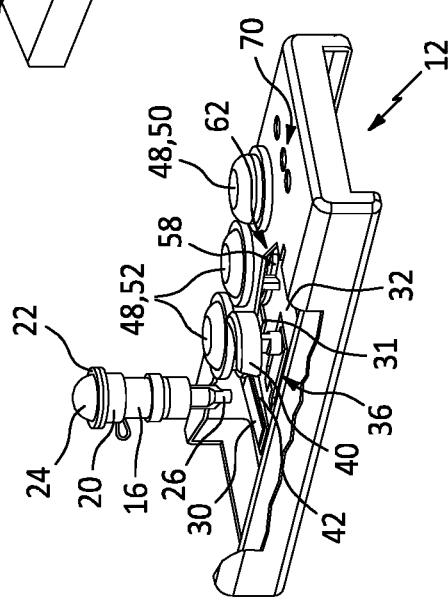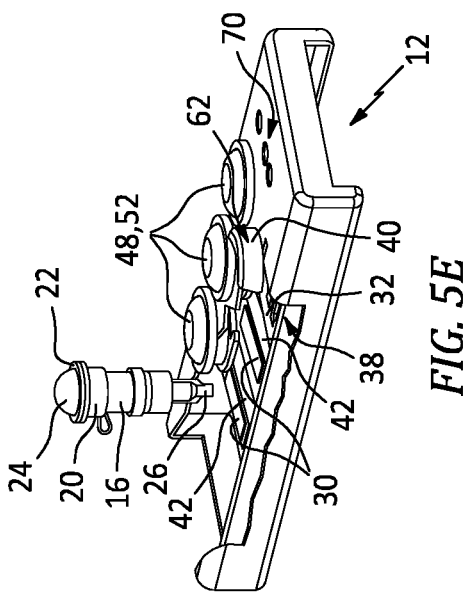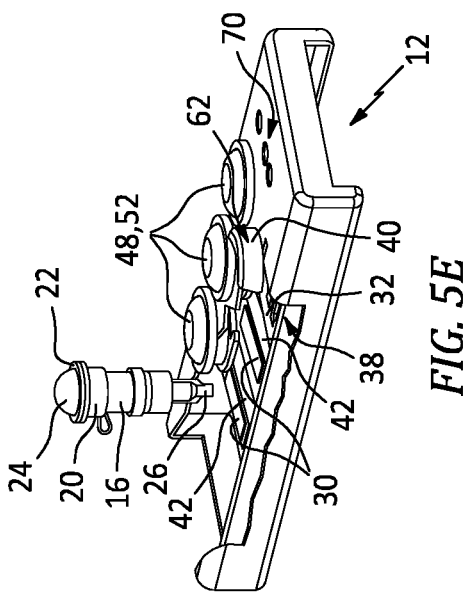

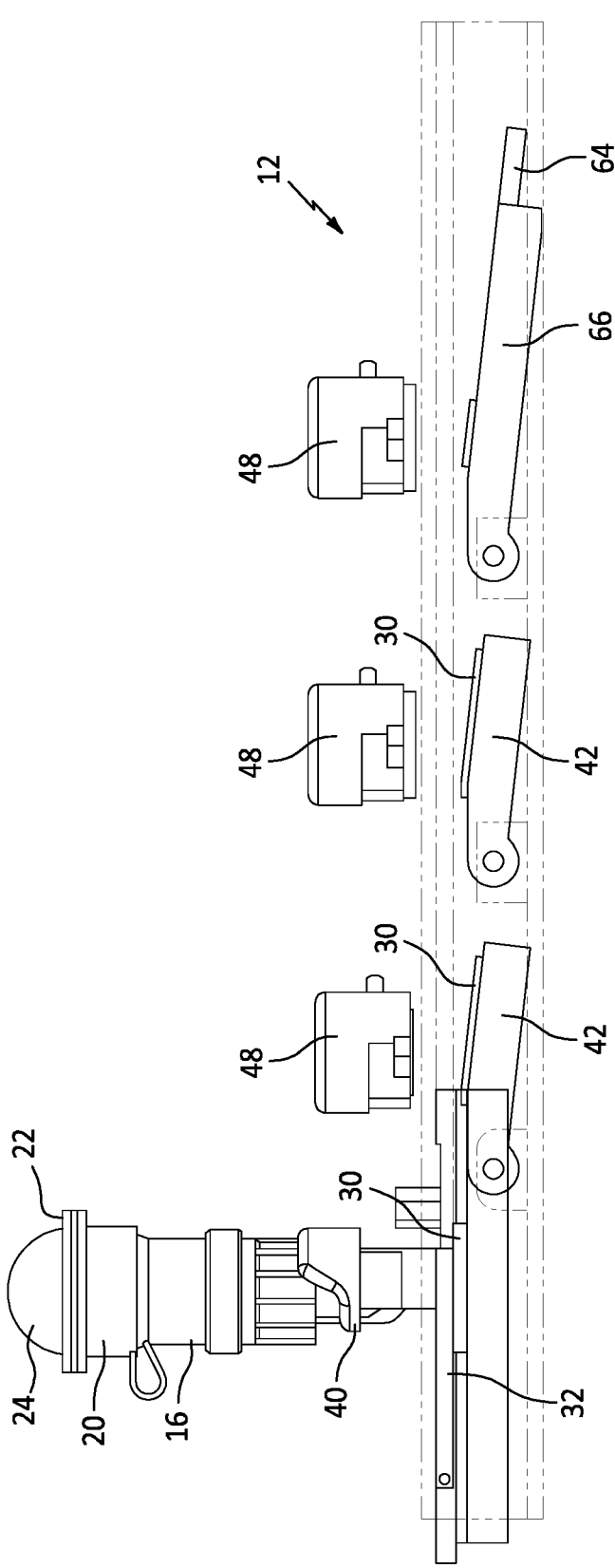
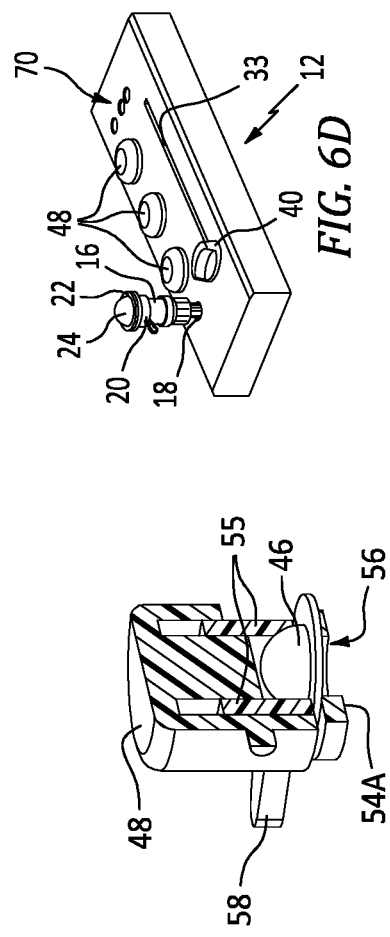
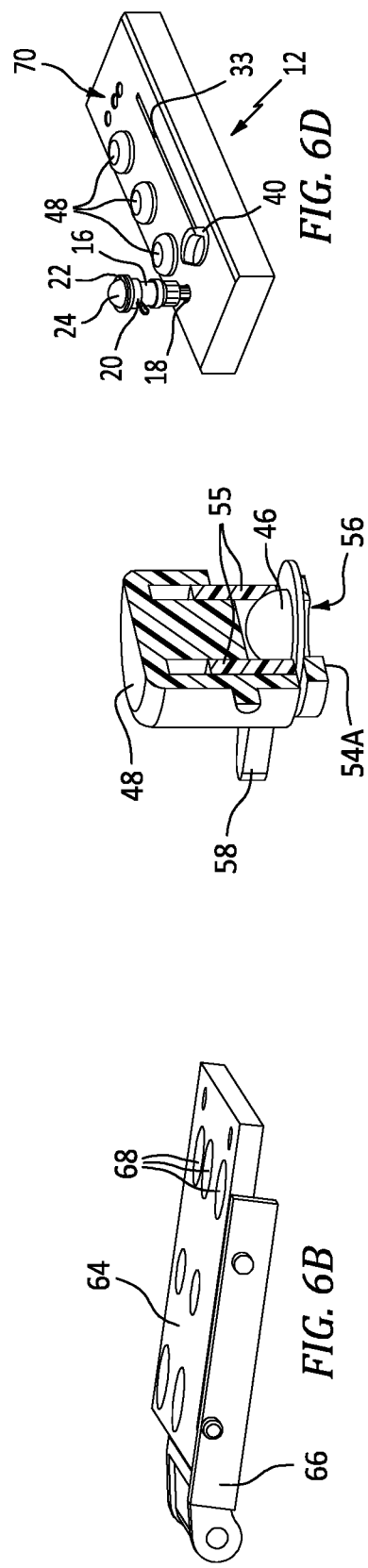

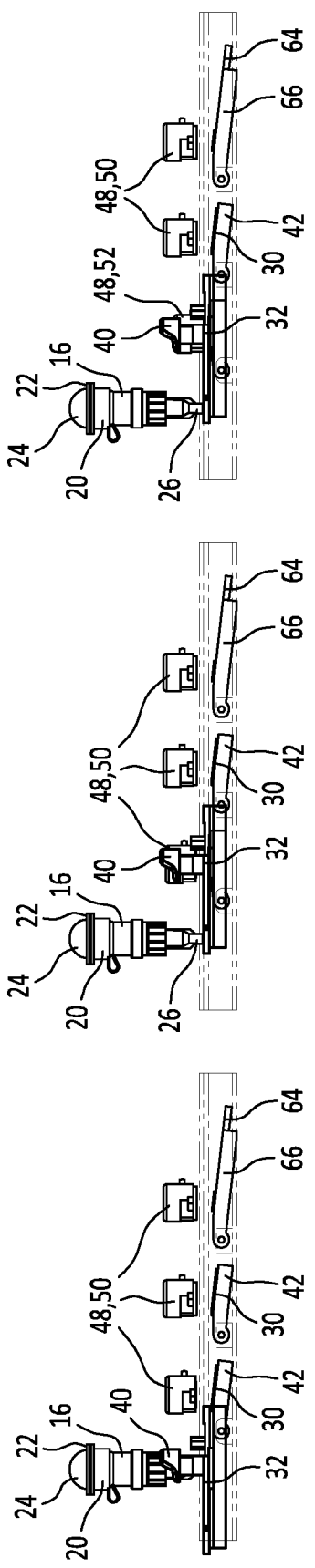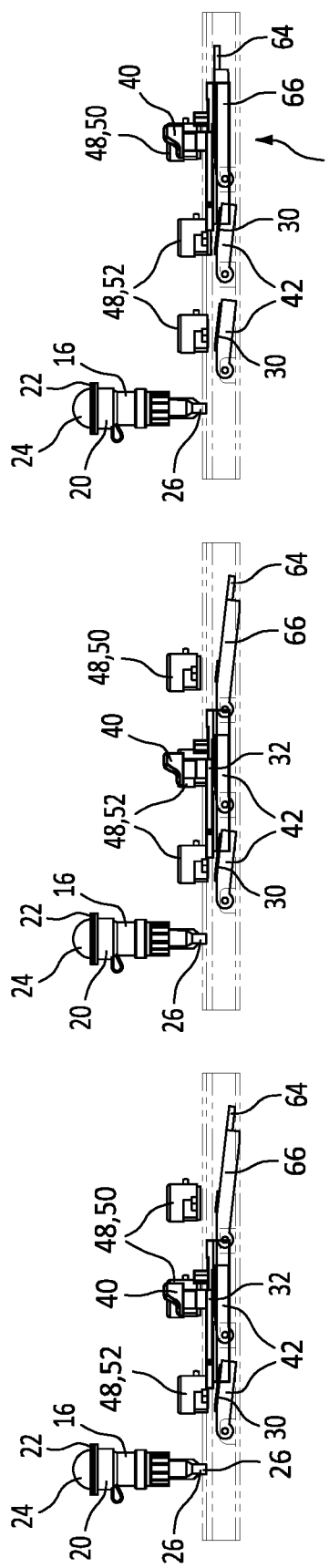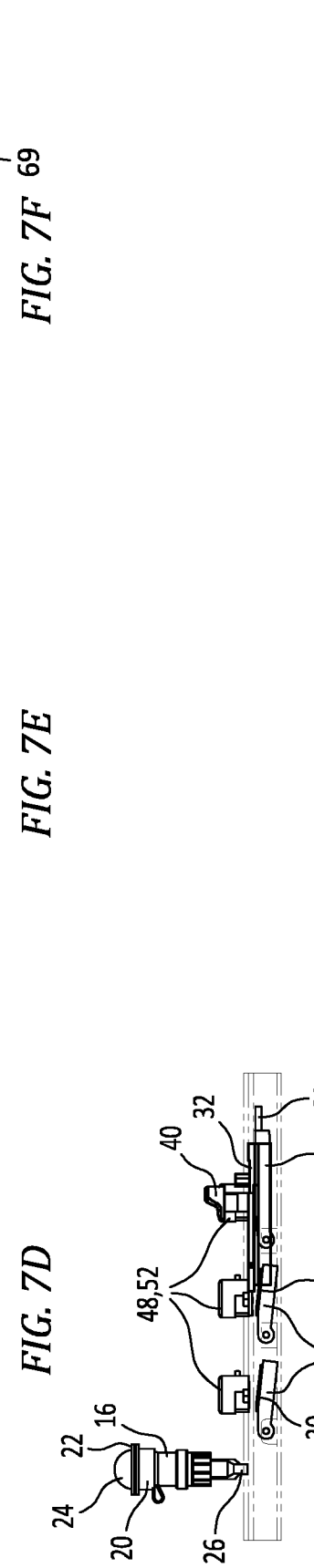

Negative

Positive

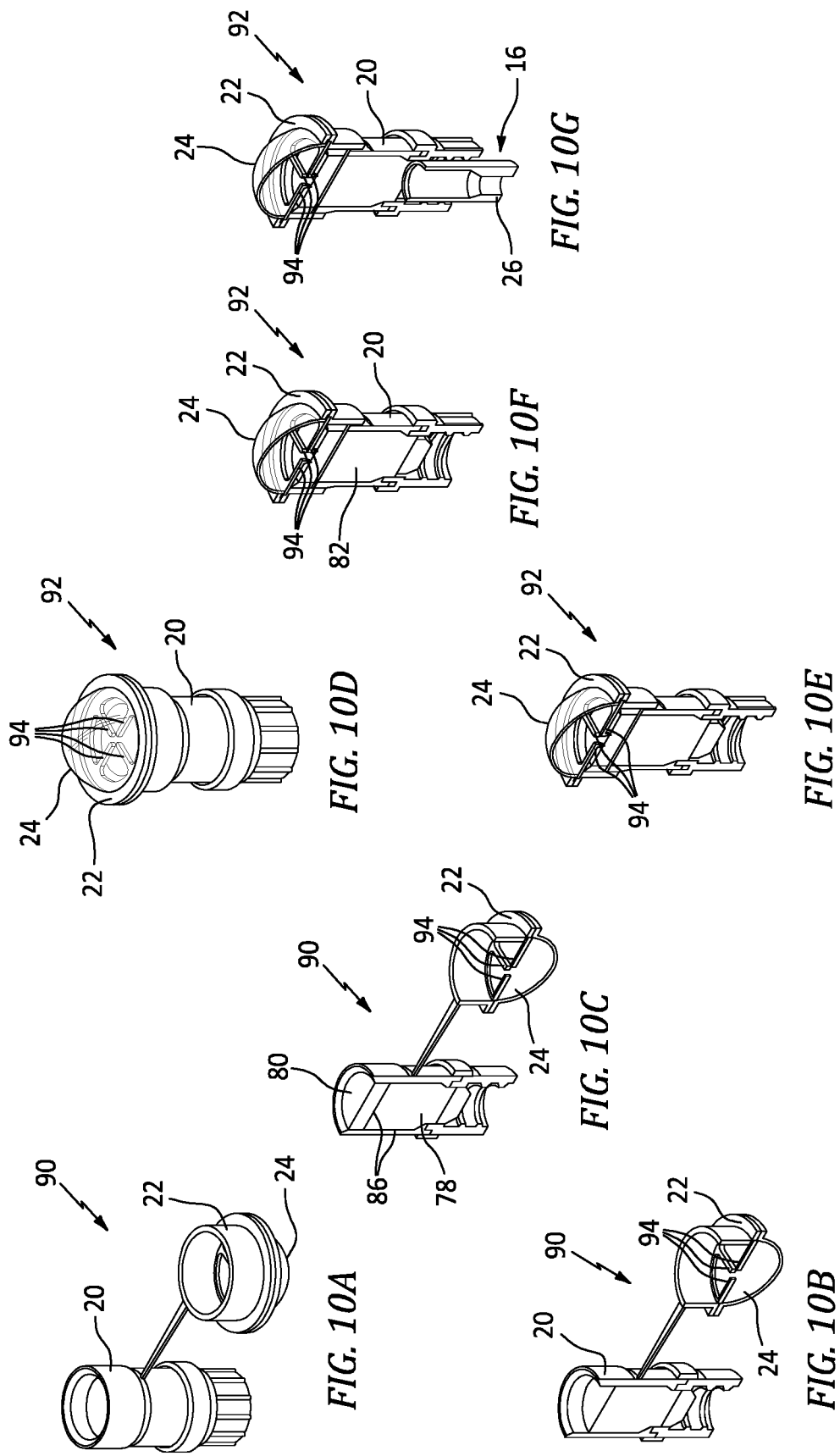

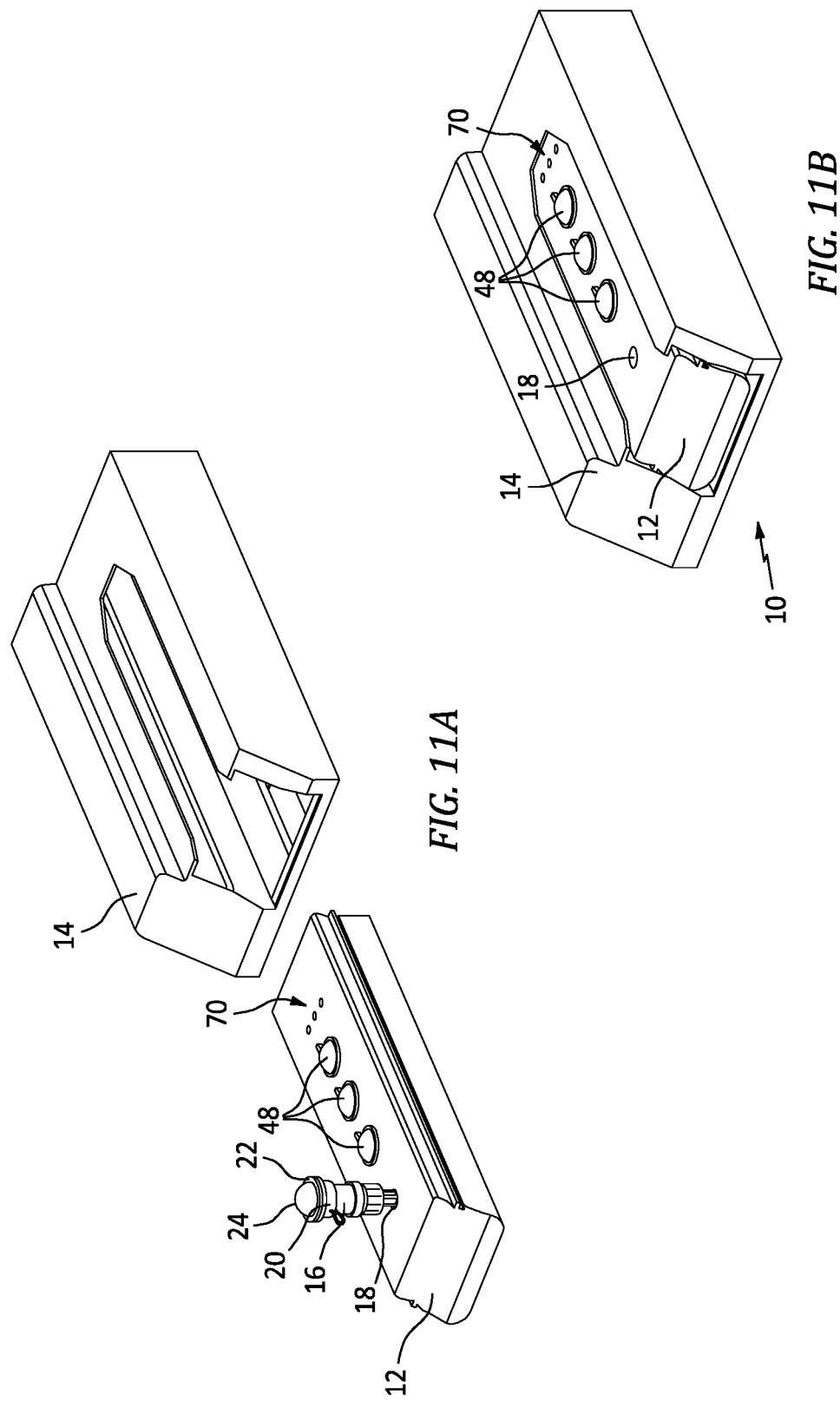

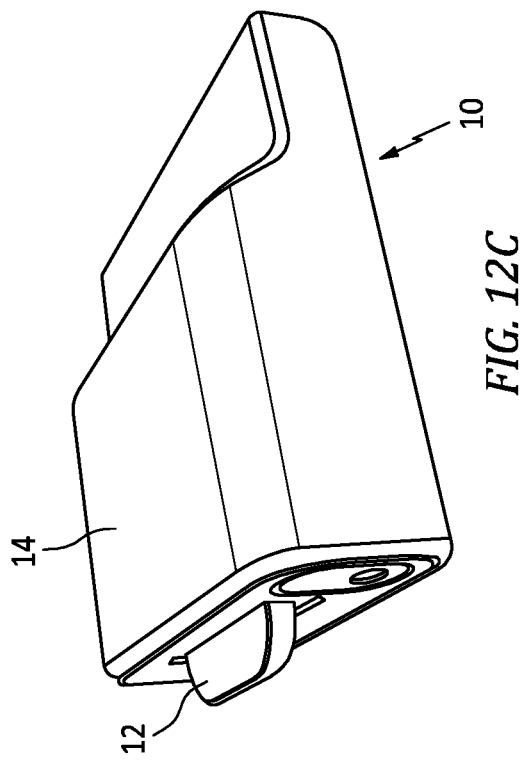
FIG. 12C
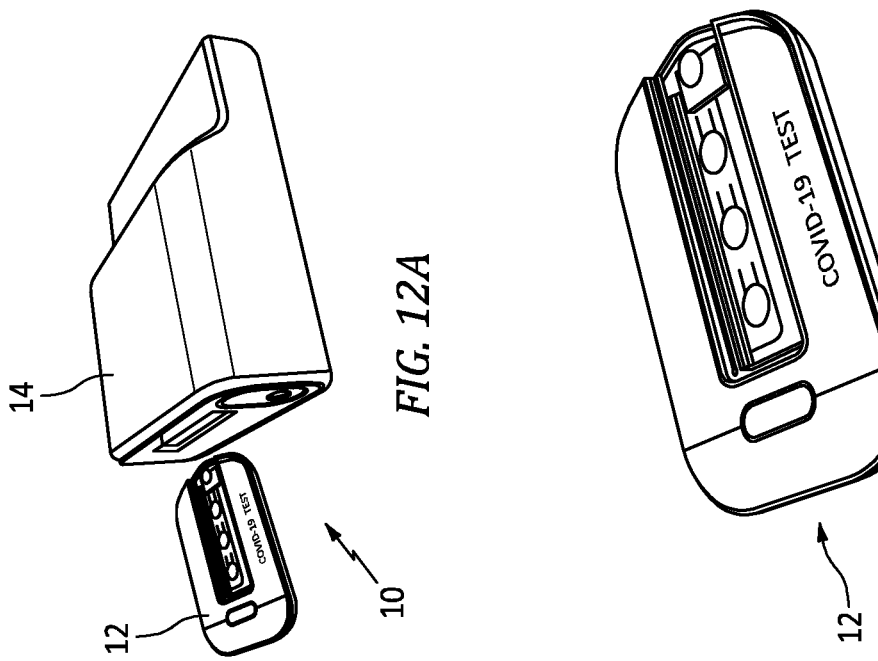
FIG. 12A
FIG. 12B

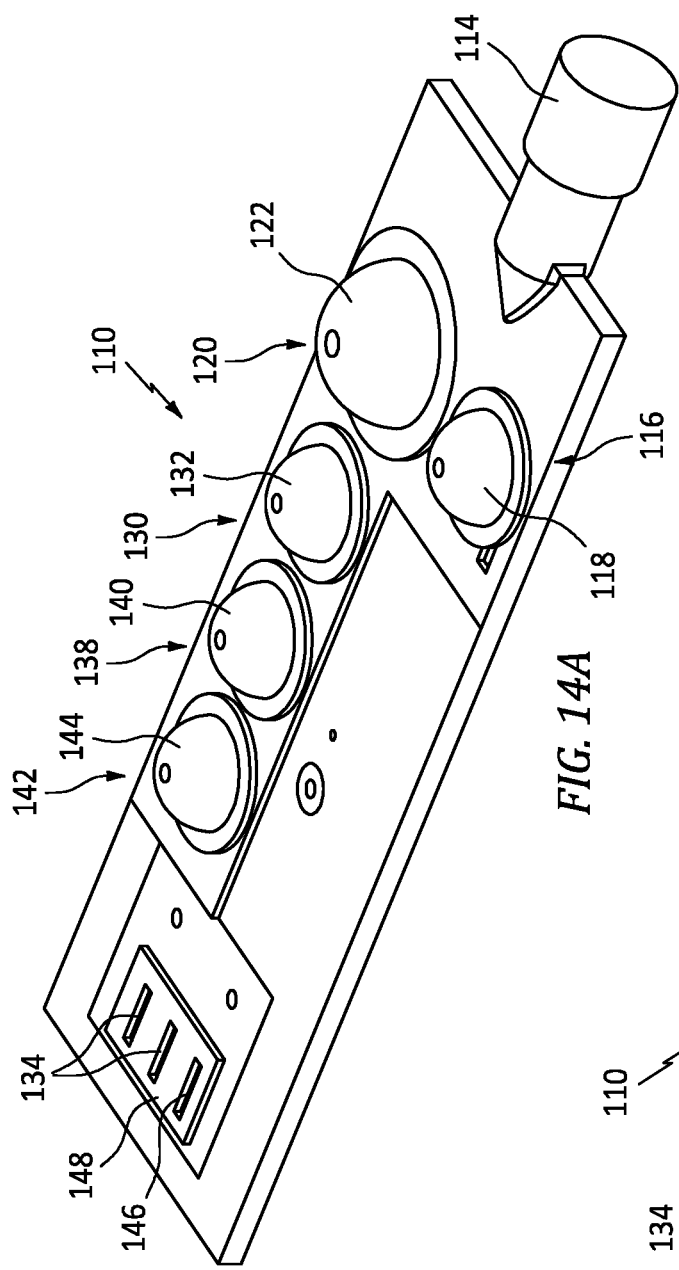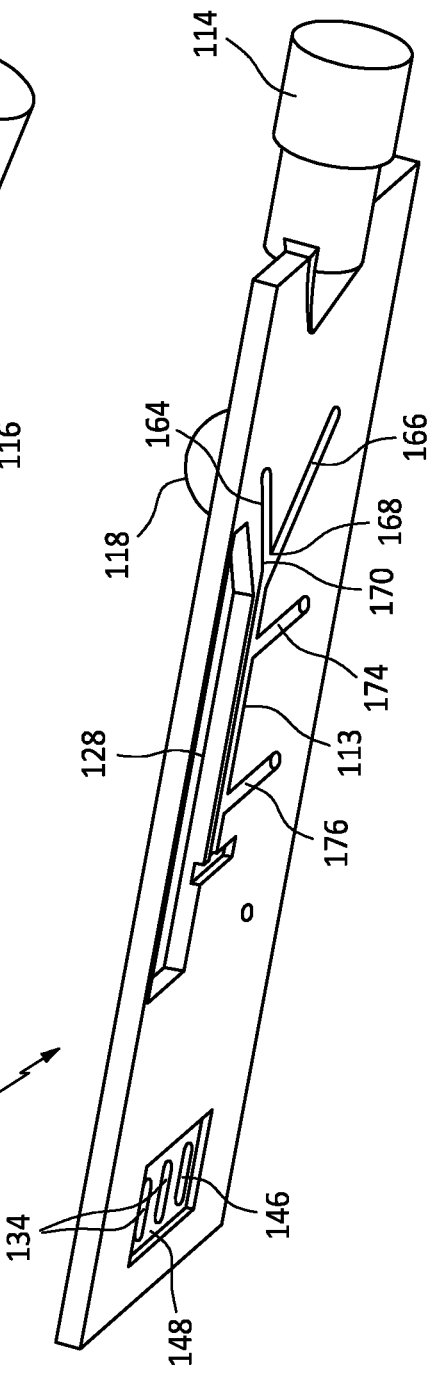
FIG. 14A
FIG. 14B

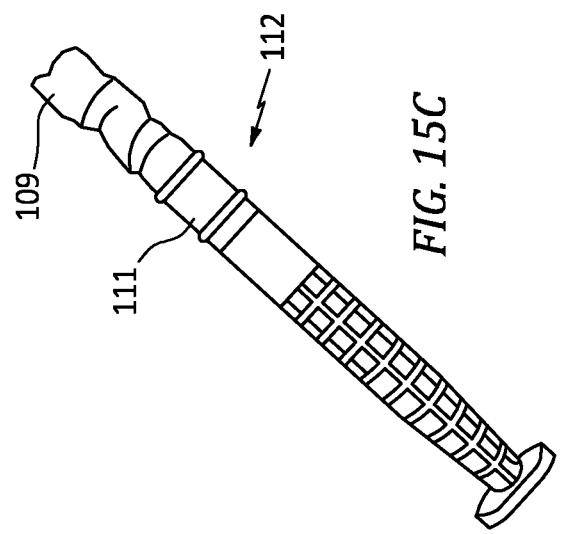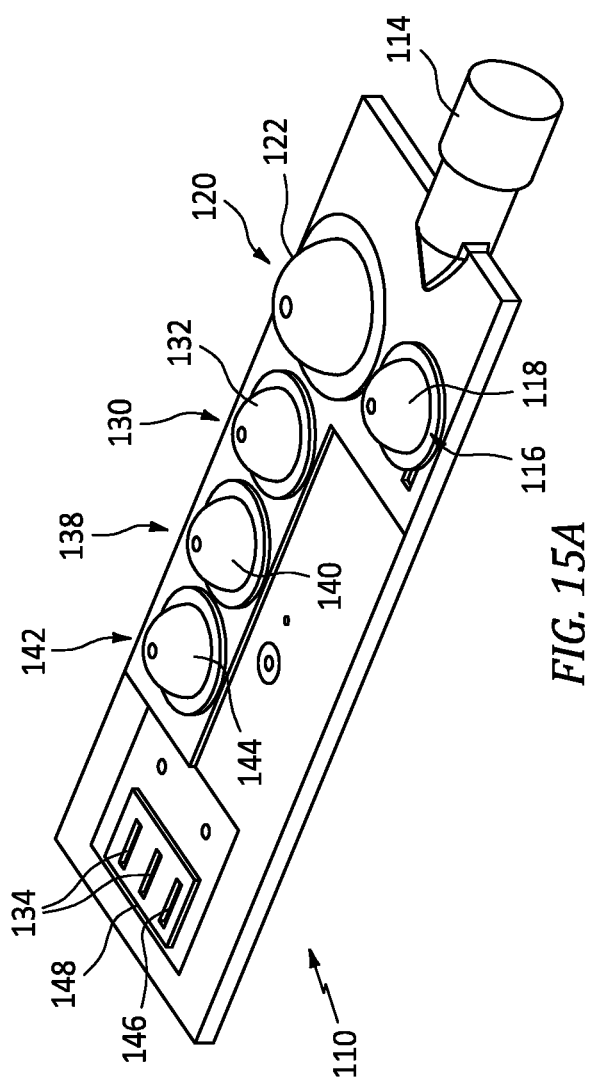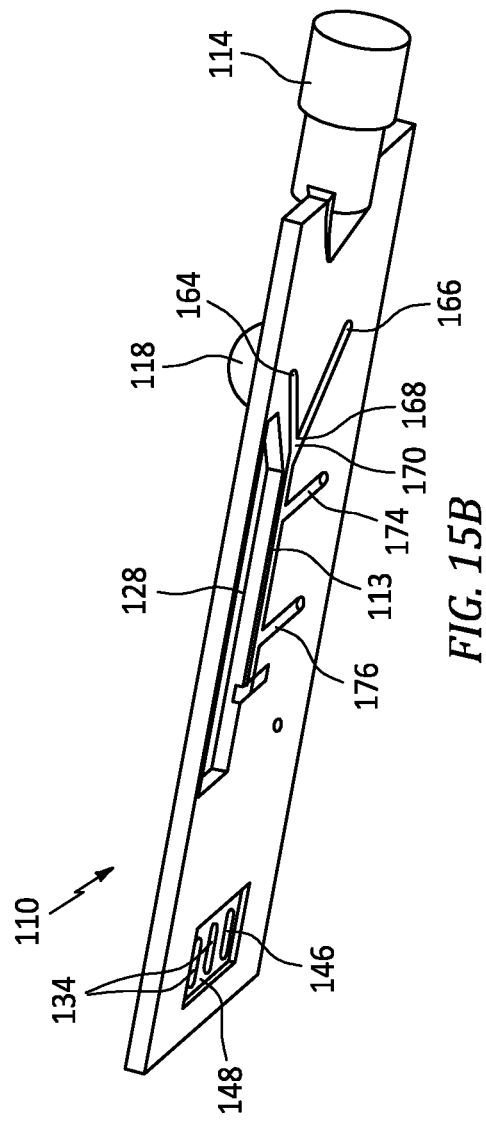

DEVICE AND METHOD FOR DETECTING NUCLEIC ACIDS IN BIOLOGICAL SAMPLES

CROSS-REFERENCE TO PRIORITY PROVISIONAL APPLICATIONS

This patent application claims priority to provisional patent application No. 63/136,435, filed Jan. 12, 2021, entitled "Device and Method for Detecting Nucleic Acids in Biological Samples," provisional patent application No. 63/154,217, filed Feb. 26, 2021, entitled "Device and Method for Detecting Nucleic Acids in Biological Samples," and provisional application No. 63/243,005, filed Sep. 10, 2021, entitled "Device and Method for Detecting Nucleic Acids in Biological Samples," each of which is hereby incorporated by reference in its entirety as part of the present disclosure.

FIELD OF THE INVENTION

The present invention is directed to devices for and methods of isolating, concentrating, amplifying and detecting nucleic acids in biological samples, such as saliva, blood, or urine samples, and more particularly, to such devices or methods including solid-state membranes and microfluidic reaction chambers.

BACKGROUND INFORMATION

A prior art isothermal nucleic acid amplification reactor with an integrated solid-state membrane is shown in U.S. Pat. No. 9,796,176 ("the '176 patent"). The '176 patent discloses a microfluidic cassette that integrates nucleic acid capture, concentration, purification, isothermal amplification, and real-time fluorescence detection into a single reaction chamber. As shown in FIG. 11 of the '176 patent, a Flanders Technologies Associates or FTA™ membrane plug is mounted at the base of the reaction chamber, and pouches 1, 2 and 3 are connected to the reaction chamber above the FTA membrane. The total volume of the reaction chamber is about 20 µl. Sample material is added to the reaction chamber. Lysis buffer in pouch 1 is added to the reaction chamber by compressing pouch 1. The lysate mixture is incubated for a prescribed time, with optional stirring by magnetic rods that may be turned by a rotating magnet. Next, an absorbent sink pad is contacted to the FTA membrane, which wicks in lysed sample to the absorption sink pad. Nucleic acid is adsorbed on the FTA membrane plug. Next, pouch 2 is compressed to add wash buffer to the reaction chamber. Then, the absorbent pad is again contacted to the FTA membrane to wick the wash buffer through the membrane. Next pouch 3 is compressed to fill the chamber with molecular or de-ionized water. The chamber is then heated by an external heating element or by chemical heating (exothermic reaction). The heating releases pre-stored, encapsulated reagents for isothermal nucleic acid amplification. This can be achieved by encapsulating the dry reagents with low melting point paraffin, which melts upon heating the reaction chamber to the desired incubation temperature (e.g., 60° C.) and releases the reagents for amplification. The amplification step proceeds at elevated temperatures for about 20-60 minutes. After amplification, a lateral flow strip is contacted to a porous membrane plug of the reaction chamber. This is made of a material that has low nucleic acid binding. The strip is loaded with amplification product, which is functionalized with antibody or antigen to capture the labeled amplicon. The LF strip loading pad contains reporter particles to enhance detection of product captured on the strip.

One drawback associated with the above-described prior art is that the solid-state membrane is fixedly mounted within a fixed fluid conduit to the reaction chamber, and the biological sample, lysate mixture and wash buffers are first introduced into the reaction chamber, and then wicked through the membrane and absorbed by the absorbent sink pad. As a result, the volumes of the biological sample, lysate mixture and wash buffers are limited by the capacity of the reaction chamber and absorbent sink pad. As indicated above, the total volume of the reaction chamber is about 20 This limits the ability to add higher sample volumes in order to increase the ability to detect targets that may be in small or low concentrations in the original sample. The small volume limits the amount of sample which can be tested and decreases the ability of the test to detect dilute or low concentration nucleic acid targets. Yet another potential drawback is that the reaction chamber may contain dry reagents encapsulated in a low-melting point paraffin for release during the heating and nucleic acid amplification step. Because the lysed sample and the wash buffers must all flow through the reaction chamber, the lyophilized reagents must be sealed in paraffin to prevent premature hydrolyzation and the loss of reagent before the reaction. The paraffin may upset the purity of the reagents and reduce the sensitivity of the assay. In addition, the encapsulated reagents contained within the reaction chamber may further limit the available volume of the reaction chamber for the above-described fluids required for the preceding steps. As a result, smaller volumes of biological samples may be passed across the membrane, and lesser amounts of target nucleic acids may be captured, purified and amplified, than desired. Yet another drawback is that the capture, purification and amplification of lesser amounts of targeted nucleic acids than desired, may lead to less sensitive and/or accurate detection of, and testing for, such targeted nucleic acids. In other words, it would be desirable for a device or method to allow for greater volumes of biological samples to be passed across such a membrane, to in turn allow for the capture of greater amounts of targeted nucleic acids to thereby improve the ability to detect such nucleic acids. It would also be desirable to have a system that does not require paraffin or like sealant to prevent hydrolyzation.

It is an object of the present invention, and/or of the currently preferred embodiments thereof, to overcome one or more of the above-described drawbacks and/or disadvantages of the prior art.

SUMMARY OF THE INVENTION

In accordance with a first aspect, the present invention is directed to a device for amplifying nucleic acids in a biological sample, such as saliva, to allow for detection of such amplified nucleic acids. The device comprises a sample port for receiving therein the biological sample, a lysis chamber including a lysis agent therein, a mixing chamber for mixing the biological sample and lysis agent into a sample-lysis mixture, one or more wash stations including a wash solution therein, and an elution station including an eluent therein. A solid-state membrane is located downstream of the mixing chamber, wash station and elution station, and is configured to capture nucleic acids in the biological sample passed across the membrane. A waste chamber is located downstream of the solid-state membrane, and one or more reaction chambers are also located downstream of the solid-state membrane. The sample port, lysis chamber and mixing chamber are configured to mix the sample and lysis agent to form a sample-lysis mixture, pass the sample-lysis mixture across the solid-state membrane to capture nucleic acids in the biological sample therein, and receive the remainder of the sample-lysis mixture in the waste chamber. The wash station is configured to introduce the wash solution across the solid-state membrane to purify nucleic acids captured therein, and receive the wash solution from the solid-state membrane in the waste chamber. The elution station is configured to pass the eluent across the solid-state membrane, elute captured nucleic acids from the solid-state membrane, and pass the captured nucleic acids into the reaction chamber for amplifying the captured nucleic acids. The amplified nucleic acids may be detected by visibly observing the reaction chamber, such as through a transparent window or other portion of the reaction chamber, and detecting a color change or other surrogate marker indicative of the amplified nucleic acids. Alternatively, the amplified nucleic acids may be passed through or outside of the reaction chamber for detection, such as into a viewing window or chamber in fluid communication with the reaction chamber.

In some embodiments of the present invention, the device further comprises a sample conduit defining the mixing chamber therein. The sample conduit is in fluid communication between each of the sample port, the lysis chamber and the wash station or wash stations, and the solid-state membrane. If desired, a lyophilized reconstitution chamber may be provided in fluid communication between the solid-state membrane and each reaction chamber. The sample port, lysis station and sample conduit are configured to mix the sample and lysis agent to form the sample-lysis mixture, pass the sample-lysis mixture across the solid-state membrane to capture nucleic acids in the biological sample therein, and receive the remainder of the sample-lysis mixture in the waste chamber. The wash station is configured to introduce the wash solution into the sample conduit following the sample-lysis mixture, pass the wash solution across the solid-state membrane to purify nucleic acids captured therein, and receive the wash solution from the solid-state membrane in the waste chamber. The elution station is configured to pass the eluent across the solid-state membrane and elute captured nucleic acids from the solid-state membrane. If one or more lyophilized reconstitution chambers are provided, the captured nucleic acids pass through the lyophilized agent reconstitution chamber and into the reaction chamber for amplifying the captured nucleic acids. Alternatively, the captured nucleic acids may pass into a combined reaction and reconstitution chamber where the lyophilized agent is added to the reaction chamber, reconstituted with the eluted nucleic acids, and subsequently amplified. In some such embodiments, the mixing chamber is defined by a mixer, such as a static mixer, located within the sample conduit in fluid communication between a sample-lysis junction and the solid-state membrane, that mixes the sample and lysis agent and forms the sample-lysis mixture prior to passage across the solid-state membrane. In one exemplary embodiment, the static mixer is defined by a plurality of axially-spaced recesses or grooves formed in the sample conduit.

Some embodiments of the present invention further comprise (i) a lysis leg extending in fluid communication between the lysis station and the sample conduit and configured to direct a flow of the lysis agent from the lysis station into the sample conduit, and (ii) a wash leg extending in fluid communication between the wash station and the sample conduit at a point upstream relative to the lysis leg and configured to direct a flow of the wash solution from the wash station into the sample conduit behind the sample-lysis mixture. In some embodiments, the wash leg is in fluid communication with the sample conduit at a sample-wash junction located adjacent to the sample port and is configured to allow a substantial portion of the sample to flow into the sample conduit downstream of the sample-wash junction prior to introducing the wash solution through the wash leg and into the sample conduit. Also in such embodiments, the lysis leg is in fluid communication with the sample conduit at a sample-lysis junction located downstream of the sample-wash junction and is configured to allow the lysis agent to mix with the sample and form the sample-lysis mixture and the wash solution to flow into the sample conduit behind or upstream of the sample-lysis mixture.

Some embodiments of the present invention further comprise a second wash station in fluid communication with the sample conduit and including a second wash solution therein. The second wash station is configured to introduce the second wash solution into the sample conduit following the other wash solution and to pass the second wash solution across the solid-state membrane to purify nucleic acids captured therein. The second wash solution passed across the solid-state membrane also is received in the waste chamber. In some such embodiments, the second wash station includes a sealed second wash chamber containing the second wash solution. A second wash leg extends in fluid communication between the second wash station and the sample conduit downstream of the other wash leg, and is configured to direct a flow of the second wash solution from the second wash station, into the sample conduit, and across the solid-state membrane to purify nucleic acids captured therein.

In some embodiments of the present invention, the elution station includes a sealed eluent chamber containing the eluent and an elution leg extending in fluid communication between the elution station and the solid-state membrane. The eluent chamber is configured to release the eluent from the eluent chamber through the elution leg and across the solid-state membrane, in order to elute captured nucleic acids from the solid-state membrane and pass the captured nucleic acids into the reaction chamber.

Some embodiments of the present invention further comprise a waste chamber vent in fluid communication between the waste chamber and ambient atmosphere. The waste chamber vent defines an open condition and a closed condition. In the open condition, fluid passing across the solid-state membrane is received within the waste chamber. In the closed condition, fluid passing across the solid-state membrane is prevented from passing into the waste chamber. In some such embodiments, during passage of the sample-lysis mixture and wash solution across the solid-state membrane, the waste chamber vent is in the open condition and the sample-lysis mixture and the wash solution passing across the solid-state membrane flow into the waste chamber and are prevented from flowing into the reaction chamber. Some embodiments of the present invention further comprise a waste vent seal movable between (i) an open position allowing fluid to flow out of the waste chamber vent and thereby allow fluid to flow into the waste chamber, and (ii) a closed position sealing the vent and thereby preventing fluid from flowing into the waste chamber.

Some embodiments of the present invention further comprise a reaction chamber valve in fluid communication between the solid-state membrane and the reaction chamber. The reaction chamber valve (i) is closed to prevent fluid flow into the reaction chamber when a fluid pressure between the solid-state membrane and the reaction chamber valve is below a valve-opening pressure, and (ii) is open to allow fluid flow into the reaction chamber when the fluid pressure between the solid-state membrane and the reaction chamber valve is above the valve-opening pressure. In some such embodiments, closure of a waste chamber vent, or movement of a waste chamber vent seal into a closed position, causes the fluid pressure between the solid-state membrane and reaction chamber valve to exceed the valve-opening pressure and thereby allow fluid flow from the solid-state membrane into the reaction chamber and not into the waste chamber.

Some embodiments of the present invention further comprise a saliva collection swab for collecting saliva thereon and receivable within the sample port for introducing the saliva directly into the sample port and sample conduit for mixture with the lysis agent.

Some embodiments of the present invention further comprise a body where the solid-state membrane and/or the body is movable relative to the other. In some such embodiments, at least the solid-state membrane is movable relative to the body from (i) a sample position where the solid-state membrane is in fluid communication with the sample port for receiving across the solid-state membrane the biological sample and capturing nucleic acids in the biological sample therein, (ii) to a wash position where the solid-state membrane is in fluid communication with the wash station for the passage of the wash solution across the solid-state membrane to purify nucleic acids captured therein, and (iii) to a reaction position where the solid-state membrane is in fluid communication with the reaction chamber for eluting captured nucleic acids from the solid-state membrane into the reaction chamber and amplifying captured nucleic acids. Some such embodiments comprise a plurality of wash stations. In such embodiments, the solid-state membrane and/or the body is movable relative to the other from the sample position to a plurality of successive wash positions. In each wash position, the solid-state membrane is in fluid communication with a respective one of the plurality of wash stations for the passage of a respective wash solution across the solid-state membrane to purify nucleic acids captured therein.

In some embodiments of the present invention, the body further includes an absorbent waste pad in fluid communication with the waste chamber and engageable with the solid-state membrane in the sample position for absorbing therein fluid passed through the solid-state membrane in the sample position and/or engageable with the solid-state membrane in the wash position(s) for absorbing therein the wash solution passed through the solid-state membrane in the wash position(s). Some such embodiments further comprise a waste pad support movably mounted on the body and including the waste pad mounted thereon. The waste pad is movably engageable with an underside of the solid-state membrane to facilitate engagement of the solid-state membrane and waste pad. Some embodiments of the present invention further comprise a membrane support including the solid-state membrane mounted thereon, a microfluidic chip defining a microfluidic reaction chamber, and a microfluidic chip support movably mounted on the body and including the microfluidic chip mounted thereon. The microfluidic chip is engageable with the solid-state membrane and/or membrane support upon movement of the solid-state membrane into the reaction position, to facilitate fluid communication between the solid-state membrane and the microfluidic reaction chamber. In some embodiments of the present invention, the membrane support and/or body is movable relative to the other from the sample position to the wash position, and from the wash position to the reaction position. In some such embodiments, the membrane support includes a manually-engageable portion, such as a knob or button, that is manually engageable to move the membrane support and membrane thereon from the sample position to the wash position, and from the wash position to the reaction position.

In some embodiments of the present invention, the lysis station, wash station and/or elution station includes a sealed chamber containing a lysis agent, wash solution or eluent, and an actuator, such as a button actuator or plunger, movable between a non-actuated position and an actuated position. In the actuated position, the lysis agent, wash solution or eluent is released from the sealed chamber. In some such embodiments, the actuator is manually engageable and moveable from the non-actuated position to the actuated position. The sealed chamber includes a frangible or breakable wall, such as formed by a blister or foil, that is breakable by the actuator in the actuated position to release the lysis agent, wash solution or eluent from the sealed chamber.

In some embodiments of the present invention, the membrane support and/or body is movable relative to the other from the sample position to the wash position, and from the wash position to the reaction position. The actuator includes a locking member movable between a locked position preventing actuation of the actuator, and an unlocked position allowing the actuator to be moved from the non-actuated position to the actuated position. The locking member is engageable with the membrane support upon relative movement into the wash position or reaction position, to thereby move the locking member from the locked position to the unlocked position. In some such embodiments, the locking member is pivotally or rotatably mounted on the body and is engageable with the membrane support. Upon movement of the membrane support into the wash positon or reaction position, the membrane support causes the locking member to rotate from the locked position to the unlocked position, and thereby allow actuation in the respective position.

Some embodiments of the present invention further comprising (i) a disposable cartridge containing the sample port, wash station, elution station, solid-state membrane, waste chamber and reaction chamber, and (ii) a base station configured to receive the disposable cartridge therein and including a heat source for facilitating a reaction in the microfluidic reaction chamber.

Some embodiments of the present invention further comprise a sample receptacle including therein a lysis fluid and configured to receive therein the biological sample for mixture with the lysis fluid. The sample receptacle includes an outlet port connectable in fluid communication with the sample port for releasing a lysis fluid and biological sample mixture into the sample port and onto the solid-state membrane. The sample receptacle includes a sealed chamber containing the lysis fluid, and a frangible or breakable wall configured to be ruptured after receiving the biological sample therein, to allow mixture of the lysis fluid and biological sample. In some of such embodiments, the sample receptacle includes a closure movable between an open position for allowing introduction of the biological sample into the sample receptacle, and a closed position sealing the biological sample and lysis fluid within the receptacle. One or more protuberances are engageable with the frangible or breakable wall when the closure is in the closed position to break the frangible or breakable wall and thereby mix the lysis fluid with the biological sample. The sample receptacle may further include a pump that is manually engageable to pump the lysis fluid and sample mixture through the outlet port and into the sample port.

In accordance with another aspect, the present invention is directed to a device comprising (i) first means for receiving therein a biological sample; (ii) second means for sealing a lysis agent therein and releasing the lysis agent therefrom for mixture with the biological sample; (iii) third means for mixing the biological sample and lysis agent into a sample-lysis mixture; (iv) fourth means for sealing a wash solution therein and releasing the wash solution therefrom; (v) fifth means for sealing an eluent therein and releasing the eluent therefrom; (vi) sixth means in fluid communication with the third means for receiving the sample-lysis mixture and capturing nucleic acids in the biological sample therein, in fluid communication with the fourth means for receiving the wash solution following the sample-lysis mixture and passing the wash solution across the sixth means for purifying nucleic acids captured therein, and in fluid communication with the fifth means for receiving the eluent across the sixth means for eluting captured nucleic acids from the sixth means; (vii) seventh means located downstream of the sixth means for receiving the remainder of the sample-lysis mixture that passes through the sixth means and the wash solution that passes through the sixth means as waste and storing the waste therein; and (viii) eighth means located downstream of the sixth means for receiving the eluted captured nucleic acids from the sixth means and for amplifying the captured nucleic acids therein.

In some such embodiments, (i) the first means is sample port; (ii) the second means is a sealed lysis chamber containing a lysis agent therein and including a frangible or breakable wall that is breakable to release the lysis agent therefrom; (iii) the third means is a sample vial connectable in fluid communication with the sample port, or a sample conduit in fluid communication with the sample port and including a static mixer therein; (iv) the fourth means is a sealed wash solution chamber containing a wash solution therein and including a frangible or breakable wall that is breakable to release the wash solution therefrom; (v) the fifth means is a sealed eluent chamber containing an eluent therein and including a frangible or breakable wall that is breakable to release the eluent therefrom; (vi) the sixth means is a solid-state membrane; (vii) the seventh means is a waste chamber in fluid communication with the solid-state membrane for receiving the remainder of the sample-lysis mixture that passes through the solid-state membrane and the wash solution that passes through the solid-state membrane as waste and storing the waste therein; and (viii) the eighth means is a microfluidic reaction chamber.

Some embodiments of the present invention further comprise means for closing the seventh means after receiving the lysis agent and wash solution therein, and for opening the eighth means for directing the captured nucleic acids from the sixth means therein.

In accordance with another aspect, the present invention is directed to a method of capturing nucleic acids in a biological sample and amplifying the captured nucleic acids therein in a reaction chamber. The method comprises the following steps:
(i) passing a biological sample and lysis fluid mixture across a solid-state membrane and capturing nucleic acids in the biological sample in the solid-state membrane;
(ii) preventing the flow of the sample-lysis mixture that passes across the solid-state membrane into the reaction chamber, and receiving the remainder of the sample-lysis mixture that passes across the solid-state membrane in a waste chamber;
(iii) passing a wash solution across the solid-state membrane and purifying nucleic acids capturing therein;
(iv) preventing the flow of the wash solution that passes across the solid-state membrane into the reaction chamber, and receiving the remainder of wash solution that passes across the solid-state membrane in the waste chamber; and
(v) passing an eluent across the solid-state membrane and eluting captured nucleic acids from the solid state membrane, directing the eluted captured nucleic acids from the solid-state membrane into the reaction chamber and not into the waste chamber, and amplifying captured nucleic acids therein in the reaction chamber.

In some embodiments of the present invention, step (i) includes introducing a lysing agent into a sample conduit, mixing the lysing agent with the sample to form a sample-lysis mixture, passing the sample-lysis mixture across the solid-state membrane, and capturing nucleic acids in the biological sample therein. In some embodiments of the present invention, steps (iii) and (iv) include introducing a wash solution into the sample conduit following the sample-lysis mixture, passing the wash solution across the solid-state membrane and purifying nucleic acids captured from the sample-lysis mixture therein, preventing the flow of the wash solution into the reaction chamber, and receiving the wash solution that passes through the solid-state membrane in the waste chamber. In some embodiments of the present invention, step (v) includes introducing an eluent across the solid-state membrane, eluting captured nucleic acids from the solid-state membrane, substantially preventing the captured nucleic acids from flowing into the waste chamber, directing the captured nucleic acids into the reaction chamber, and amplifying the captured nucleic acids in the reaction chamber.

Some embodiments of the present invention further comprise closing a vent to the waste chamber after receiving the lysis agent and wash solution therein, and opening an inlet valve to the reaction chamber for directing the captured nucleic acids from the solid-state membrane therein.

In some embodiments of the present invention, step (iii) includes moving the solid-state membrane and/or a first washing station relative to the other into a first wash position, step (v) includes moving the solid-state membrane and/or a microfluidic reaction chamber relative to the other into a reaction position, eluting captured nucleic acids from the solid-state membrane into the microfluidic reaction chamber, and amplifying captured nucleic acids therein. Some embodiments further comprise moving the solid-state membrane, and/or a support for the solid-state membrane, into a reaction position. Then, upon moving the solid-state membrane or support therefor into the reaction position, moving a microfluidic chip containing the microfluidic reaction chamber into engagement with an underside of the solid-state membrane and/or the support therefor, and placing the microfluidic reaction chamber in fluid communication with the solid-state membrane.

Some embodiments of the present invention further comprise introducing a cartridge containing the biological sample and lysis fluid, solid-state membrane, wash solution, eluent and chamber, into a base station, performing at least step (v) with the cartridge located in the base station, and disposing of the cartridge after use.

One advantage of the present invention, and/or of embodiments thereof, is that the lysis mixture and sample is passed across the solid-state membrane, and the wash solution is passed across the solid state membrane, all prior to connecting the solid-state membrane in fluid-communication with the microfluidic reaction chamber. Accordingly, the volume of the biological sample, and the volume of lysing agent and/or washing solution(s) passed across the solid-state membrane, are not limited by the relatively small volume of the microfluidic reaction chamber and/or capacity of a single adsorbent pad, as encountered in the above-described prior art. As a result, the device and method of the present invention allow for larger volumes of biological samples and provide for a correspondingly greater capture of targeted nucleic acids. This, in turn, allows for a more sensitive detection of targeted nucleic acids and more accurate testing for such nucleic acids. Yet another advantage is that the device and method of the invention, and/or of the embodiments thereof, allow for even significantly greater amounts of biological samples, lysis fluids and/or wash solutions as compared to prior art devices and methods, particularly as compared to prior art hand-held or mobile devices or methods. Yet another advantage is that the components of the device and method can be provided in a cartridge that can be mounted in a base station to heat the microfluidic reaction chamber and/or otherwise facilitate the amplification and detection of the captured nucleic acids. A still further advantage is that each cartridge can be disposed of after use and the base station can be reused with additional cartridges to conduct additional tests. A further advantage is that the use of paraffin or like sealants to prevent premature hydrolyzation and the loss of reagent before the reaction as required by the above-described prior art can be avoided.

Other objects and advantages of the present invention, and/or of embodiments thereof, will become more readily apparent in view of the following detailed description of embodiments and accompanying drawings.

BRIEF DESCRIPTION OF THE DRAWINGS

FIGS. 3A through 3I are a series of perspective views of the cartridge and sample vial of FIGS. 1 and 2 illustrating the following procedural steps: (i) in FIGS. 3A and 3B, loading a saliva sample from the sample vial into the sample receptacle of the cartridge, (ii) in FIGS. 3C and 3D, washing the sample, (iii) in FIGS. 3E and 3F, washing the sample again, (iv) in FIGS. 3G and 3H, eluting the DNA/RNA into the reaction chamber, and (v) in FIG. 3I, incubating the reaction chamber, e.g., at about 62° C. for about 20 minutes, and then comparing the color of the reaction chamber fluid to a test chip to determine if targeted nucleic acids are detected;

FIGS. 5A through 5E include a series of perspective, cut-away views of the cartridge and sample vial of FIGS. 1 and 2 illustrating the following additional procedural steps: (5) in FIG. 5A, the sample vial received in the sample port of the cartridge, and in FIG. 5B, manual movement of the membrane slider from the first wash station toward the second wash station, and disengagement of the first wash waste pad from the underside of the membrane slider; (6) in FIG. 5C, manual advancement of the membrane slider to the second wash station and alignment of the membrane slider with the second wash station blister and waste sump/pad; (7) in FIG. 5D, unlocking of the second blister plunger in the second wash station to, in turn, allow the second blister plunger to be manually depressed to break the blister and wash the captured nucleic acids in the solid-state membrane in the second wash station; and (8) in FIG. 5E, disengagement of the second wash waste pad from the underside of the membrane slider and manual movement of the membrane slider from the second wash station toward the reaction position in fluid communication with the reaction chamber where the third blister plunger is depressed;

FIG. 6A is a perspective, cut-away view of the cartridge of FIGS. 1 and 2, FIG. 6B is a separate perspective view of the microfluidic chip and microfluidic chip carrier, FIG. 6C is an exemplary perspective, cross-sectional view of the blister plunger and blister assembly in each wash station, and FIG. 6D is another perspective view of the cartridge and sample vial of FIGS. 1 and 2;

FIGS. 7A through 7G are a series of perspective, partial cross-sectional views of the cartridge of FIGS. 1 and 2 showing (1) in FIG. 7A, the membrane slider in fluid communication with the sample port, (2) in FIG. 7B, movement of the membrane slider into the first wash station, (3) in FIG. 7C, unlocking of the blister plunger in the first wash station and engagement of the first waste pad with the underside of the membrane slider for absorbing the wash solution in the first wash station, (4) in FIG. 7D, disengagement of the first wash waste pad and movement of the membrane slider from the first wash station into the second wash station, (5) in FIG. 7E, unlocking of the blister plunger in the second wash station and engagement of the second wash waste pad with the underside of the membrane slider for absorbing the wash solution in the second wash station, (6) in FIG. 7F, disengagement of the second wash waste pad and movement of the membrane slider from the second wash station into the reaction position, (7) in FIG. 7G, unlocking of the blister plunger in the reaction position and engagement of the microfluidic reaction chamber with the underside of the membrane slider for placing the microfluidic reaction chamber in fluid communication with the solid-state membrane in the reaction position;

FIGS. 10A through 10G are a series of the following views: (1) FIGS. 10A and 10B are a perspective view and a perspective cross-sectional view, respectively, of the sample vial as received and ready for receiving a sample, (2) FIG. 10C is a perspective, cross-sectional view of the sample vial after receiving a sample therein, such as a saliva sample, and its closure in an open position, (3) FIGS. 10D and 10E are a perspective view and a perspective cross-sectional view, respectively, of the sample vial with its closure in the closed position; (4) FIG. 10F is a cross-sectional view of the sample vial after the protuberances or piercing members of the closure break the sealed chamber of the vial containing lysis fluid, and gentle agitation thereof to mix the sample and lysis fluid within the vial, and (5) FIG. 10G is a perspective, cross-sectional view illustrating insertion of the outlet port and valve of the sample vial into the sample port of the cartridge of FIGS. 1 and 2 so that the dome-shaped pump of the closure may be depressed to, in turn, pump the sample-lysis fluid mixture into the sample port and solid-state membrane in fluid communication therewith;

FIGS. 11A and 11B are two perspective views of the cartridge and base station of FIGS. 1 and 2, including in FIG. 11A the cartridge prior to insertion into the base station, and in FIG. 11B the cartridge inserted into the base station;

FIGS. 12A through 12C include perspective views of another embodiment of a cartridge and base station for amplifying and detecting nucleic acids in a biological sample wherein the cartridge includes the solid-state membrane near the distal end thereof, and the base station includes the wash station(s) and microfluidic reaction chamber(s) (not shown), and illustrating in FIG. 12A the cartridge prior to insertion into the base station, in FIG. 12B the cartridge itself, and in FIG. 12C the cartridge inserted into the base station;

FIGS. 14A and 14B include upper and lower perspective views, respectively, of a device embodying the present invention including a disposable cartridge that is received within a base station for amplifying and detecting nucleic acids in a biological sample;

FIGS. 15A and 15B include upper and lower perspective views, respectively, of the device of FIGS. 14A and 14B, and FIG. 15C is a partial, perspective view of a saliva collection syringe-type device receivable within the sample port of the device of the device of FIGS. 14A and 14B for introducing a saliva sample therein;

DETAILED DESCRIPTION

Figure 1:
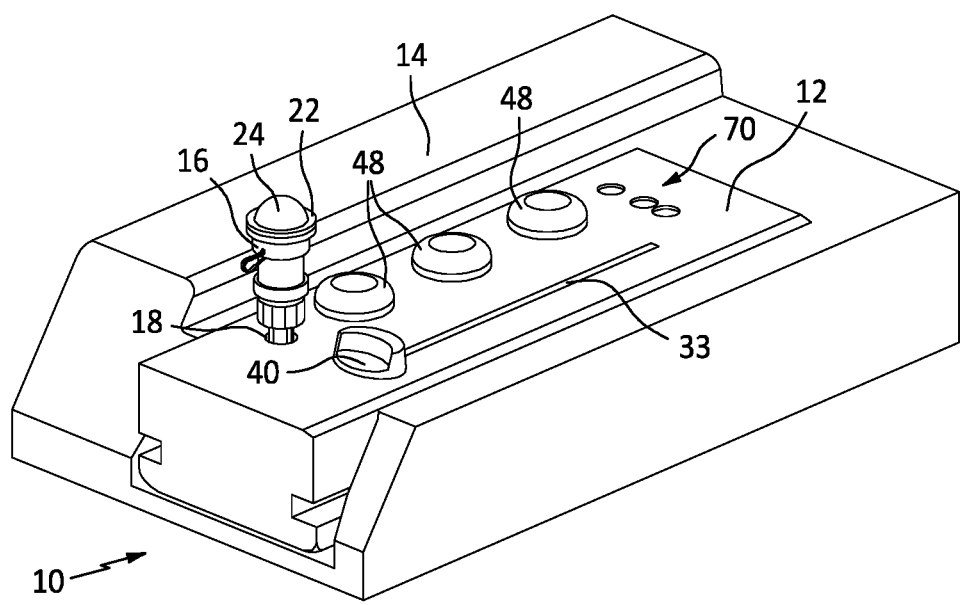
FIG. 1 includes a perspective view of a device embodying the present invention including a disposable cartridge received within a base station for amplifying and detecting nucleic acids in a biological sample.

In FIG. 1, a device embodying the present invention for amplifying and detecting nucleic acids in a biological sample is indicted generally by the reference numeral 10. The device 10 can be used to identify target nucleic acid sequences corresponding to target pathogen or host genetic sequences including any genetic target in a biological or environmental sample. Identification is done through the isolation, concentration, isothermal amplification, and detection of nucleic acids. Multiple targets can be identified simultaneously. Examples of use include without limitation: (i) the detection of infectious agents such as SARS-CoV-2, in saliva, swab, urine, or stool; (ii) the detection of specific mutations in blood samples; and (iii) the detection of infectious agents from a surface swab. The device 10 in FIG. 1 comprises a body or test cartridge 12, a base station 14, and a sample receptacle or vial 16. A biological sample will be placed into the sample vial 16 and combined with a lysis chemistry facilitating cell lysis, releasing any nucleic acids from cells in the biological sample. The sample vial 16 is inserted into a sample port 18 of the test cartridge 12. The sample and lysis chemistry mixture is extruded from the sample vial 16 into the sample port 18 of the test cartridge 12.

Figure 2A:
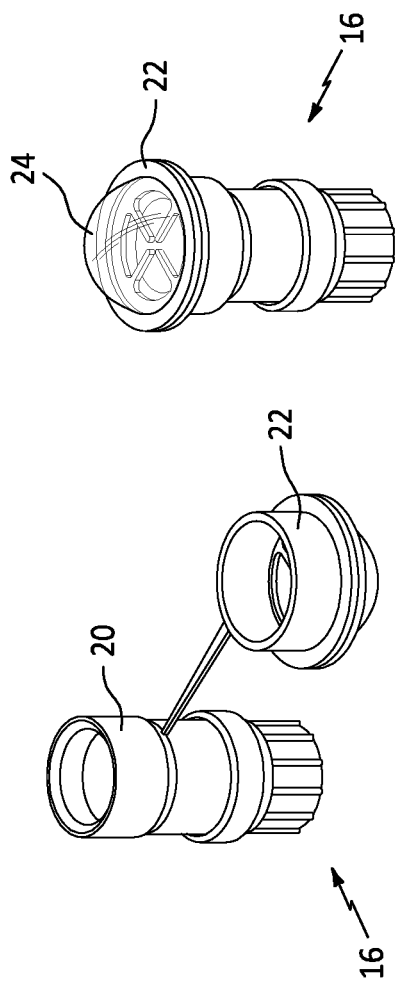
FIGS. 2A through 2C include (i) in FIG. 2A, a perspective view of a sample receptacle or vial for biological sample collection and lysis, including a left-hand view showing the vial open, and a right-hand view showing the vial closed, (ii) in FIG. 2B, a perspective view of a disposable cartridge for amplifying and detecting nucleic acids in a biological sample, and the closed sample vial suspended above the cartridge and ready to supply a sample and lysis mixture to the cartridge for testing, and (iii) in FIG. 2C, a perspective view of the cartridge including the sample vial with the outlet port thereof connected in fluid communication with the sample port of the cartridge, and the cartridge received within the base station for capturing, concentrating, purifying, amplifying and detecting targeted nucleic acids in the biological sample.
Figure 2C:
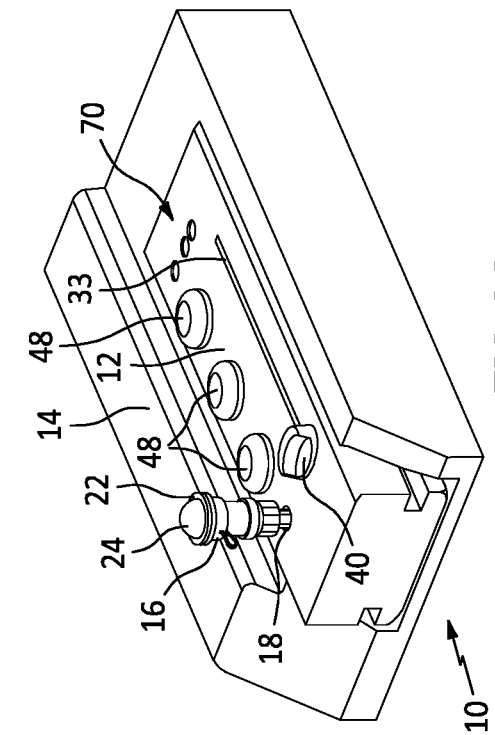
Figure 2B:
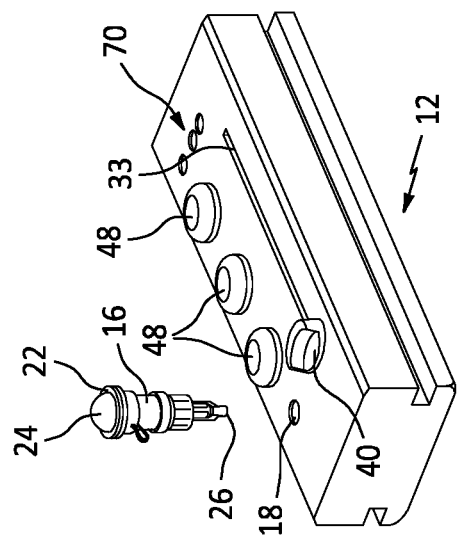
Figure 4A:
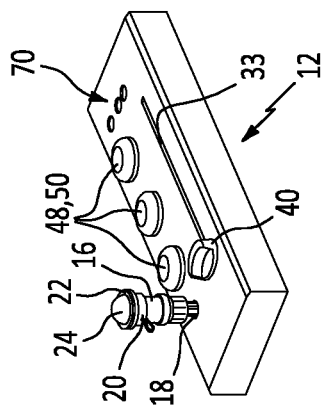
FIGS. 4A through 4E include a series of perspective, cut-away views of the cartridge and sample vial of FIGS. 1 and 2 illustrating the following procedural steps: (1) in FIG. 4A, the sample vial received in the sample port of the cartridge, and in FIG. 4B, the sample waste sump/waste pad engaged with the underside of the solid-state membrane slider for capturing nucleic acids from the sample in the solid-state membrane; (2) in FIG. 4C, manual advancement of the membrane slider toward the first wash station, and disengagement of the sample waste sump/waste pad therefrom; (3) in FIG. 4D, rotation of the blister plunger in the first wash station as the membrane slider is manually moved therein and engagement of the first wash waste pad with the underside of the membrane slider when received in the first wash station; and (4) in FIG. 4E, unlocking of the blister plunger in the first wash station to, in turn, allow the first blister plunger to be manually depressed to break the blister and wash the captured nucleic acids in the solid-state membrane in the first wash station.
Figure 4B:
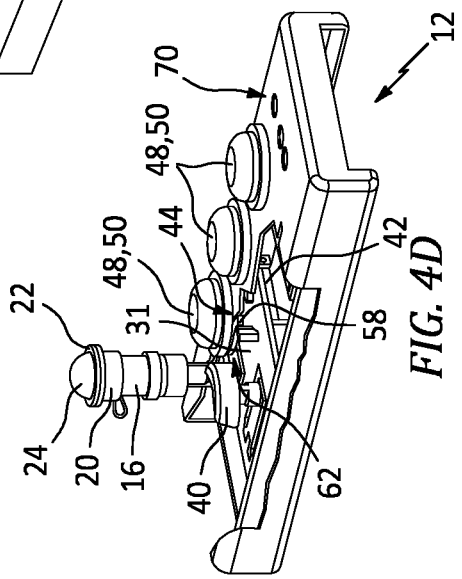
Figure 4C:
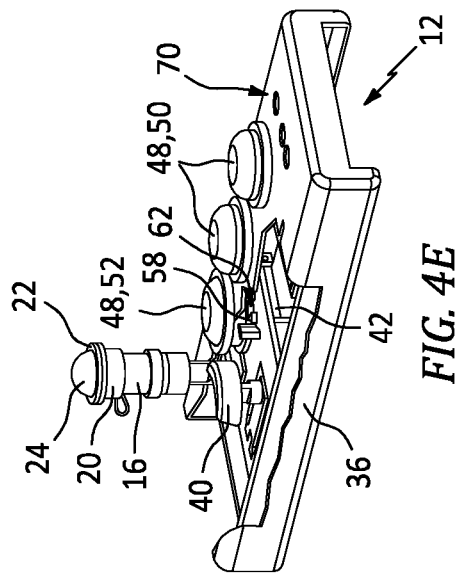
Figure 4D:
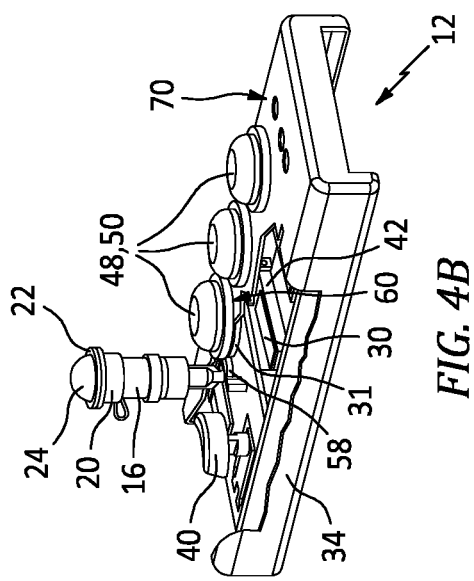
Figure 4E:
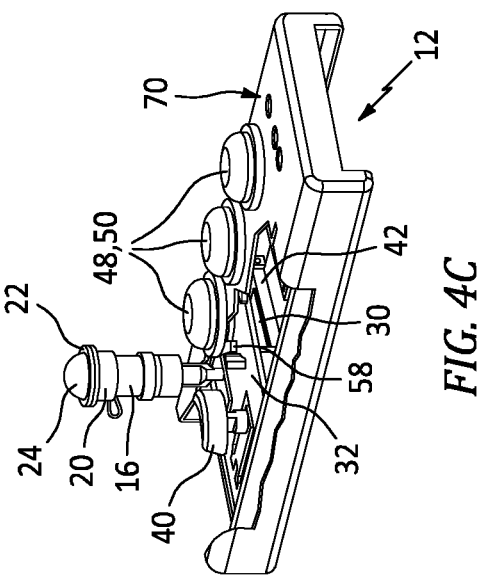

FIG. 2 shows the sample vial 16 and test cartridge 12 in greater detail. The sample vial 16 comprises a vial body 20 and a vial closure or cap 22. When the vial cap 22 is inserted onto the vial body 20, the vial cap 22 seals the sample vial 16. The vial cap 22 of the sample vial 16 comprises a dome-shaped pump 24 which can be used to pump the sample mixture through an outlet port 26 in the sample vial 16. When the sample vial 16 is inserted into a sample port 18 of the test cartridge 12, the sample will move through an outlet port 26 of the sample vial 16 to enter the test cartridge 12. The test cartridge 12 is inserted into the base station 14 for isolation, concentration, and amplification of any targeted nucleic acids in the sample.

FIGS. 3-7 show the mechanism and operation of the exemplary device 10 in greater detail. Once the sample vial 16 is inserted into the sample port 18 of the test cartridge 12, the outlet port 26 of the sample vial 16 will be placed in fluid communication with the top of a solid-state membrane 28 (shown in FIG. 4) and a waste pad 30 will be engaged with the underside of the solid-state membrane 28. The outlet port 26 is in fluid communication with the solid-state membrane 28 and the solid-state membrane 28 is in fluid communication with the waste pad 30. Fluids can pass through the solid-state membrane 28, such as by capillary action, and therefore the outlet port 26 is in fluid communication with the waste pad 30. The dome-shaped pump 24 is used to pump the sample-lysis mixture into the test cartridge 12 and across the solid-state membrane 28. Portions of the sample-lysis mixture will be adsorbed onto the solid-state membrane 28 and isolated from the remainder of the mixture, which will be absorbed by the waste pad 30. The solid-state membrane 28 is made of a capture material that binds nucleic acids, resulting in the adsorption of nucleic acids in the biological sample. In the illustrated embodiment, the membrane is defined by a solid-state structure, i.e., it does not include moving parts, and includes without limitation a solid-state filter matrix. The solid-state filter matrix may be formed of silica, glass fibers, cellulose or other materials that are currently known, or that later become known for such purpose. An exemplary capture material is the Pall A/E Borosilicate Glass Membrane without binders from Pall Corporation. Such a membrane is made of or includes borosilicate glass fibers that bind nucleic acids. However, as may be recognized by those of ordinary skill in the pertinent art based on the teachings herein, the solid-state membrane 28 may be made of any of numerous different materials and may take any of numerous different configurations that are currently known, and/or that later become known.

The solid-state membrane 28 is contained within a membrane support 31 which is, in turn, mounted on a membrane slider 32 movably mounted on the test cartridge 12. As shown in FIGS. 1-7 and 14, the membrane slider 32 is manually engageable and movable through an axially-elongated slot 33 formed in the body 12 in a direction parallel to the elongated sides of the test cartridge 12. As may be recognized by those of ordinary skill in the pertinent art based on the teachings herein, the solid-state membrane 28 may be mounted and movable within the test cartridge, or the test cartridge may be movable relative to the solid-state membrane, in accordance with any of numerous different mechanisms or configurations that are currently known, or that later become known. For example, the solid-state membrane could be mounted on a support that is rotatably mounted on the cartridge to allow the membrane to be rotated from one station or position to the next. Alternatively, as described below, the solid-state membrane may be fixedly mounted on the test cartridge or device, i.e., not movable on the device or movably mounted.

As shown in FIGS. 4-6, the membrane slider 32 begins in a sample position 34, is moved to each of a plurality of wash positions 36 and ends at a reaction position 38. The membrane slider 32 comprises a manually-engageable portion or knob 40 which is manually engageable and movable through the axially-elongated slot 33 in the test cartridge 12 to move the membrane slider 32 and membrane 28 thereon from the sample position 34 to a first wash position 36, from the first wash position to a second wash position 36, and from the second wash position 36 to the reaction position 38. A plurality of waste pad supports 42, 42 are pivotably mounted on the test cartridge 12 to support waste pads 30, 30 at the sample position 34 and each of the wash positions 36, 36. When the membrane slider 32 is located at the sample position 34, or any of the wash positions 36, the waste pad support 42 located at the respective position including a waste pad 30 pivotably mounted thereon pivots to engage with the underside of the solid-state membrane 28. Engagement of each waste pad 30 with the solid-state membrane 28 facilitates effective capillary action of the waste pad 30 on the solid-state membrane 28. As the slider 32 advances away from the sample position 34 or any of the wash positions 36, the respective waste pad support 42 and waste pad 30 located at the position disengage from the solid-state membrane 28. As may be recognized by those of ordinary skill in the pertinent art based on the teachings herein, the waste pads 30, 30 and waste pad supports 42, 42 may take any of numerous different configurations that are currently known, or that later become known, and the device may include any desired number of waste pads and/or waste pad supports. For example, while the exemplary implementation includes separate waste pads 30 and waste pad supports 42 for each of the sample position 34 and wash positions 36, 36, the device could include waste pads and waste pad supports spanning multiple positions, multiple waste pads at a single position, multiple waste pads on a single waste pad support, a single waste pad supported by multiple waste pad supports, or any combination thereof. For example, a single waste pad and waste pad support spanning the sample position and both wash positions could be employed. Alternatively, as described below, the device may include a waste chamber or receptacle without any waste pad or pads.

As the membrane slider 32 reaches each wash position 36, 36, the solid-state membrane 28 will complete a wash station 44 at that position. As shown in FIGS. 4-7, each wash station 44 comprises the solid-state membrane 28, an interlock 55 located above the solid-state membrane 28, a sealed chamber or blister 46 mounted within the interlock 55 and containing a wash solution, an actuator or blister plunger 48 mounted on the interlock 55 and movable between a non-actuated position 50 and an actuated position 52, an upper seal or sealing pad 54A (FIG. 6C) extending about the blister 46 and sealing the blister within the interlock 55, and a waste pad 30 supported by and pivotably mounted on a waste pad support 42 located on the underside of the solid-state membrane. As can be seen, the actuator or blister plunger 48 located at each wash station 36 is manually engageable and depressible from the non-actuated position 50 into the actuated position 52. When the actuator or blister plunger 48 is moved to the actuated position 52, the lower end of the actuator or blister plunger 48 engages and breaks the sealed chamber of the blister 46 to release the wash solution therein. The force exerted by the blister plunger 48 pushes the wash solution into the solid-state membrane 28 and capillary action of the waste pad 30 pulls the wash solution into the waste pad 30 to thereby purify and isolate the nucleic acids adsorbed on the solid-state membrane 28 by washing away unbound matter from the solid-state membrane.

As shown in FIG. 6C, the sealed chamber or blister 46 includes a frangible or breakable wall 56 that is configured to break as the actuator or blister plunger 48 moves into the actuated position 52, releasing the wash solution from the sealed chamber 46 and allowing it to pass across the solid-state membrane 28 to purify the nucleic acids captured therein. Movement of the plunger 48 from the non-actuated position 50 to the actuated position 52 causes the actuator or blister plunger 48 to exert pressure on the sealed chamber or blister 46. Blister rupture pins (not shown) are located below the frangible wall 56 and come in contact with and burst the frangible wall as the blister actuator 48 is compressed to release the wash solution onto the solid-state membrane 28. The upper sealing pad 54A is impermeable to the wash solution and sufficiently compressible to ensure a fluid-tight seal between the interlock 55 and the membrane slider 32. In some configurations, the upper sealing pad 54A is sufficiently compressible to facilitate a substantially complete emptying of the blister 46 upon depressing the blister plunger 48 into the fully-actuated position 52. One of ordinary skill will recognize that while the upper sealing pad 54A is attached to an actuator in FIG. 6C, it could provide the same functional benefits if attached to the membrane slider 32 or other structure.

In the exemplary implementation shown in FIGS. 4 and 5, each of the actuators 48, 48 includes a locking member 58 movable between a locked position 60 preventing actuation of the actuator 48, and an unlocked position 62 allowing the actuator 48 to be moved from the non-actuated position 50 to the actuated position 52. Each locking member 58 starts or is normally located in the locked position 60. When the membrane slider 32 moves into a respective wash position 36, 36 or the reaction position 38, the corresponding locking member 58 is engaged by the membrane slider 32 to move the locking member 58 from the locked position 60 to the unlocked position 62. The locking member 58 is pivotably or rotatably mounted on the test cartridge 12 and engageable with the membrane slider 32 such that the membrane slider 32 causes the locking member 58 to rotate from the locked position 60 to the unlocked position 62. While in this exemplary implementation each rotating locking member 58 is part of the respective actuator 48, one of ordinary skill in the relevant art will recognize that alternative locking configurations may be used including, for example, a configuration where the locking member and actuator are separate components, or where no locking member is employed at all.

Each waste pad 30, 30 is made of absorbent materials of a type known to those of ordinary skill in the pertinent art to pull the sample, washes, and other liquids across and/or through the solid-state membrane 28. Such materials allow the fluid flow to be driven by capillary forces. The action of depressing the sample vial pump 24 and/or depressing an actuator 48, 48 to the actuated position 52 may not itself generate sufficient thrust to push liquids through or across the solid-state membrane 28. Accordingly, the waste pads 30, 30 induce capillary forces to pull the liquids across the solid-state membrane 28. The membrane 28 otherwise (without contact with an absorption pad 30) may resist liquid flow, and the liquid may not fully or sufficiently pass across the solid-state membrane 28 without the absorbing waste pad 30. In the exemplary implementation shown in FIGS. 6 and 7, each waste pad 30 is lowered or dropped out of engagement with the membrane support 40 and/or solid-state membrane 28 upon movement thereof out of the respective wash station 30.

While the exemplary implementation shown allows for manual movement of the manually-engageable portion 40 of the slider and manual engagement of each actuator by the operator of the device, one of ordinary skill in the pertinent art would recognize that the device could be made with any number of manually or automatically operated mechanisms to accomplish the same or essentially the same function, including a drive mechanism, such as a screw or gear drive, that may or may not be connected or connectible to an electric motor.

FIG. 6 shows an exemplary microfluidic chip 64 pivotably mounted on a chip carrier 66 and comprising a plurality of microfluidic reaction chambers 68, 68. The microfluidic chip 64 may include a plurality of reaction chambers 68, 68, preferably about three to seven reaction chambers, and in the illustrated embodiment, includes three reaction chambers 68, 68. The chip carrier 66 is pivotably mounted to the body 12 so that when the membrane slider 32 moves into the reaction position 38, the microfluidic chip 64 engages the underside of the solid-state membrane 28. Similar to the wash stations 44, 44, a reaction station 69 (shown in FIG. 7) at the reaction position 38 is completed by movement of the solid-state membrane 28 into the reaction position 38. The reaction station 69 includes the solid-state membrane 28, the microfluidic chip 64 mounted on the chip carrier 66 underneath the solid-state membrane 28, an interlock 55 located above the solid-state membrane 28, a sealed chamber or blister 46 mounted within the interlock 55 and containing an elution buffer, an actuator or blister plunger 48 mounted on the interlock 55 and movable between a non-actuated position 50 and an actuated position 52, and the upper seal or sealing pad 54A extending about the sealed chamber or blister 46 and sealing the blister 46 within the interlock 55. As the actuator or blister plunger 48 is moved to the actuated position 52, the elution buffer is released when the lower end of the plunger engages the sealed container or blister 46, breaks the blister and thereby releases the elution buffer therein. The pressure created by depressing the blister plunger 48 and the capillary action induced by the microfluidic chip 64 cause the elution buffer to pass across the solid-state membrane 28 and into the reaction chambers of the microfluidic chip for amplification and identification. The elution buffer releases the adsorbed, purified nucleic acids from the solid-state membrane 28 as it passes through, eluting the nucleic acids into the elution buffer and carrying the nucleic acids into the microfluidic reaction chambers 68, 68.

As shown in FIG. 6C, the sealed chamber or blister 46 includes a frangible or breakable wall 56 that is configured to break when the actuator 48 moves into the actuated position 52, releasing the elution buffer from the sealed chamber 46 and allowing it to pass across the solid-state membrane 28 and carry with it the nucleic acids captured therein. Movement of the blister plunger 48 from the non-actuated position 50 to the actuated position 52 causes the plunger to exert pressure on the blister 46. Blister rupture pins (not shown) are located below the frangible wall 56 and come in contact with and burst the frangible wall as the blister actuator 48 is compressed to release the elution buffer across the solid-state membrane 28. The upper sealing pad 54A is impermeable to the elution buffer and sufficiently compressible to ensure a fluid-tight seal between the interlock 55 and the membrane slider 32. In some configurations, the upper sealing pad 54A is sufficiently compressible to facilitate a substantially complete emptying of the sealed chamber 46.

Nucleic acid amplification reagents, including primers and enzymes, are provided in the reaction chambers 68, 68 in the form of dry and stable reagents, such as lyophilized reagents, to be hydrolized when the elution buffer enters the microfluidic chip 64 and flows into the reaction chambers 68, 68. The illustrated embodiment of the device 10 employs a loop-mediated isothermal amplification ("LAMP") method of amplification. However, as may be recognized by those of ordinary skill in the pertinent art based on the teachings herein, other methods of amplification that are currently known or that later become known may be employed.

Figure 8A:
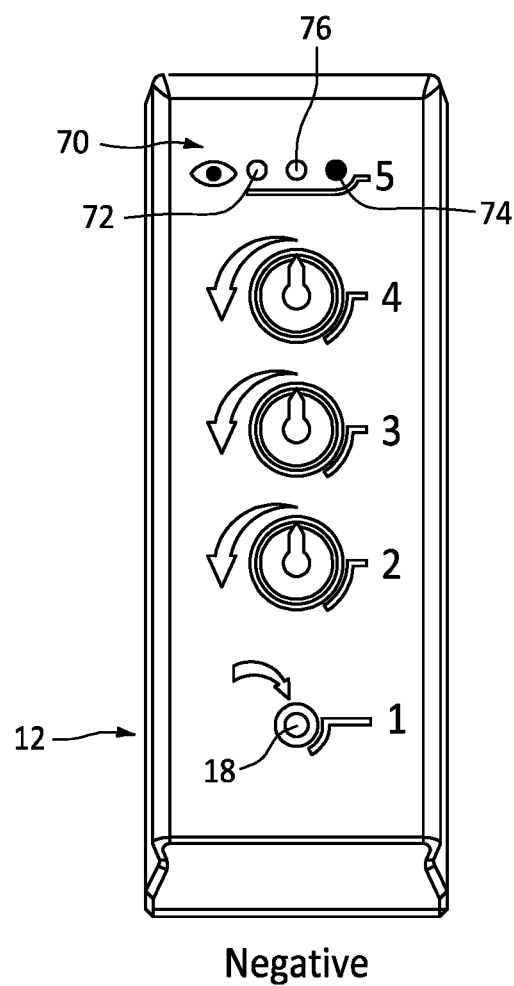
FIGS. 8A and 8B are top plan views of an exemplary front face of a cartridge of the type shown in FIGS. 1 and 2 with arrows indicating the sample port and rotational direction of the blister plungers, and showing in FIG. 8A the test windows of the cartridge indicating a negative test result, and in FIG. 8B the test windows of the cartridge indicating a positive test result.
Figure 8B:
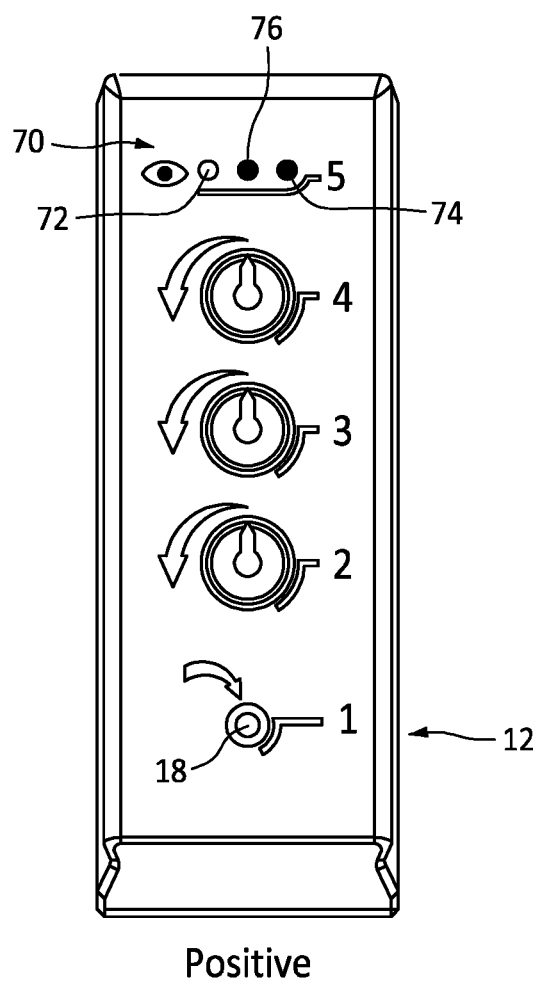

As indicated in FIGS. 11A and 11B, the device 10 may be used to detect SARS-COV-2 using a heating element (not shown) in the base station 14 to ensure that the reaction chambers 68, 68 are maintained at a substantially constant temperature for LAMP reaction at a desired temperature, such as about 63° C., when the cartridge is inserted into the base station. The base station 14 maintains the LAMP reaction temperature for a set period of time, which in the exemplary embodiment is approximately 28 minutes for the LAMP implementation detection of SARS-COV-2. As shown in FIG. 8, at the end of this period, the results of the test will be visible through a results window 70. The results window 70 contains a negative control 72, a positive control 74, and a sample indicator 76. If the color of the sample indicator 76 matches the color of the negative control 72, the test indicates a negative result. If the color of the sample indicator 76 matches the color of the positive control 74, the test indicates a positive result. The detection method is a colorimetric or fluorescent dye that can be easily seen by the user of the device 10. As may be recognized by those of ordinary skill in the pertinent art based on the teachings herein, different reaction solutions, amplification reactions, and detection methods may have different or non-isothermal ideal reaction temperatures. Accordingly, the base station 14 may be adapted to provide different reaction temperatures that may be warmer or cooler than ambient or room temperature, including cyclic variation of warmer and cooler temperatures as required for polymerase chain reaction ("PCR") amplification or other temperature settings, which are currently known or that later become known for performing such functions.

FIGS. 10A through 10G show in greater detail an embodiment of the sample receptacle or vial 16. The sample vial 16 includes a vial body 20 containing therein a lysis fluid 78 and configured to receive therein the biological sample 80 for mixture with the lysis fluid 78. An outlet port 26 of the sample receptacle 16 is configured to be inserted into the sample port 18 of the test cartridge 12 for releasing the lysis fluid and biological sample mixture 82 into the sample port 18 and across the solid-state membrane 28 in the sample position 34. The sample receptacle 16 includes a sealed chamber 84 containing the lysis fluid 78, and a frangible or breakable wall 86 configured to be ruptured after receiving the biological sample 80 therein to allow mixture of the lysis fluid 78 and biological sample 80. The sample receptacle 16 includes a cap or closure 22 movable between an open position 90 for allowing introduction of the biological sample 80 into the sample receptacle 20, and a closed position 92 sealing the biological sample 80 and lysis fluid 78 within the receptacle. One or more protuberances or piercing members 94 are engageable with the frangible or breakable wall 86 when the closure 22 is in the closed position 92 to break the frangible or breakable wall 86 and thereby mix the lysis fluid 78 with the biological sample 80. Manual agitation may be required to ensure adequate mixing of the sample 80 and lysis fluid 78. The cap or closure 22 includes an elastomeric, dome-shaped pump 24 and the piercing members 94 mounted thereon below the pump. As can be seen, the cap or closure 22 includes four piercing members 94, 94 equally spaced relative to each other and extending radially inwardly. The end of each piercing member includes a pointed protuberance or tip that projects downwardly. When the closure 22 is moved into the closed position, the tips of the piercing members 94, 94 engage the sealed chamber and break the frangible wall thereof to place the lysis fluid in fluid communication with the sample and allow mixing thereof in the sealed vial 16. The pump 24 is manually engageable to pump the mixture 82 through the outlet port 26 and into the sample port 18. As can be seen, the pump 24 includes an approximately dome-shaped or hemispherical shaped, flexible wall, which is manually engageable and depressible to pump the lysis fluid and biological sample mixture 82. One of ordinary skill in the pertinent art will recognize that alternative pump configurations can accomplish the same or similar results, and that the frangible or breakable wall 86 of the sealed chamber 84 may be broken using alternative mechanisms or configurations. The sample receptacle 16 includes an outlet valve (not shown) in fluid communication with the vial body 20. The outlet valve defines a normally-closed position preventing release of fluid from the interior of the receptacle through the outlet port, and an open position allowing fluid from the interior of the receptacle to flow through the outlet port. The outlet valve may include a valve member movable between a closed position and an open positon. The sample port 18 may include a valve-engaging member that engages the valve member when the outlet port 26 is in fluid communication with the sample port 18 to move the valve member from the closed position to the open position.

Figure 13A:
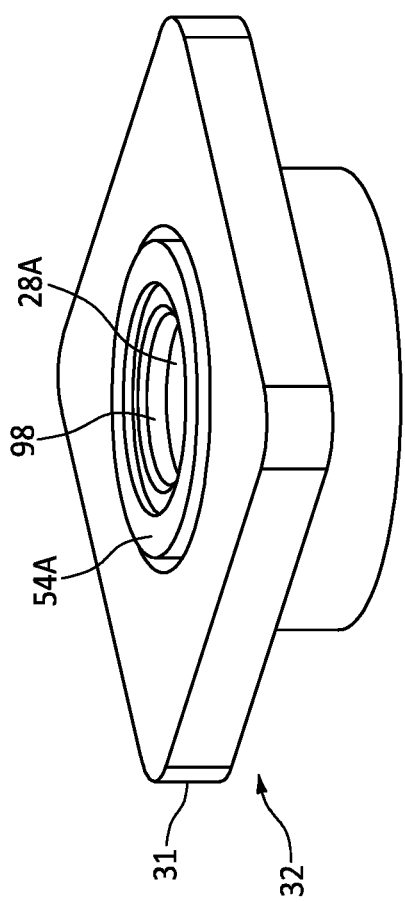
FIG. 13A is a perspective view of the membrane slider of the device of FIGS. 1-7 and including the solid-state membrane mounted therein.
Figure 13C:
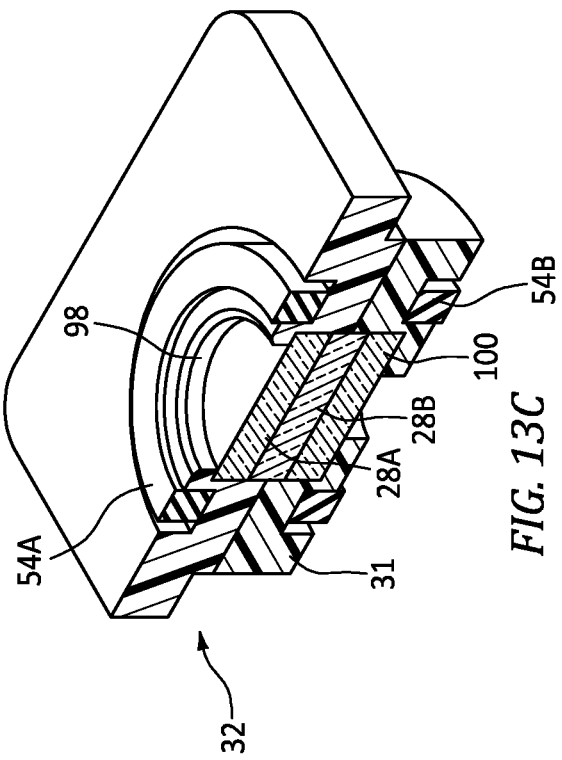
FIG. 13C is a perspective, cross-sectional view of the membrane slider and solid-state membrane of FIG. 13A.
Figure 13B:
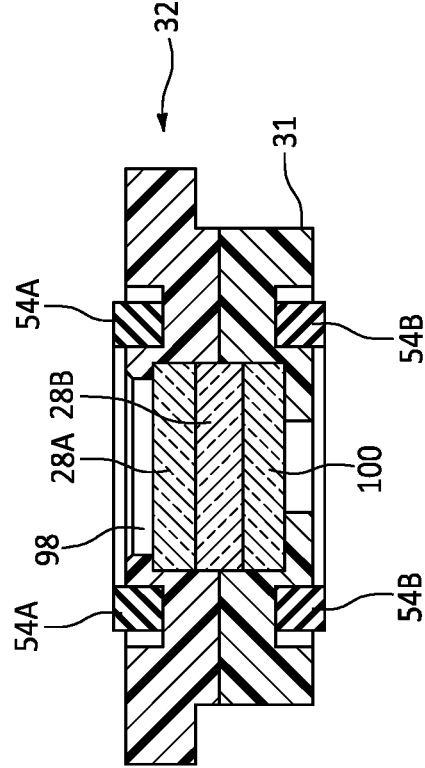
FIG. 13B is a cross-sectional view of the membrane slider and solid-state membrane of FIG. 13A.

As shown in FIGS. 13A through 13C, the membrane slider 32 comprises the membrane support 31 including the solid-state membrane 28 mounted therein. As can be seen, in the illustrated embodiment, the solid-state membrane 28 includes two layers 28A, 28B of the glass material received within an aperture 98 in the membrane support 31. A porous support 100 is mounted on the membrane support 31 below, and underlies the layers 28A, 28B of membrane material to support the membrane 28 within the membrane support 31. In the illustrated embodiment, the porous support 100 is made of a relatively rigid plastic to support the overlying layers 28A, 28B of membrane material, but is sufficiently porous to allow any fluids flowing across the membrane to pass therethrough. The porous support 100 engages the respective waste pads 30, 30 and microfluidic chip 64 in the sample position 34, wash positions 36, 36 and reaction position 38 to facilitate the flow of fluids across the membrane 28 by capillary action through the porous support and into the waste pads 30, 30 or microfluidic chip 64. As may be recognized by those of ordinary skill in the pertinent art based on the teachings herein, the solid-state membrane 28 can include any desired number of layers, and the layers may take any of numerous different thicknesses, and the porous support 100 may take the form of any of numerous different frits, sieves, grates or like structures, that are currently known, or that later become known, for performing the functions of these components. The upper peripheral seal 54A is mounted on the upper side of the membrane support 31 and surrounds the solid-state membrane 28, and a lower peripheral seal 54B is mounted on the underside of the membrane support and surrounds the underside of the membrane and porous support. As described above, the upper peripheral seal 54A sealingly engages the outlet port 26 of the sample vial 16 in the sample position 34, and extends about the blister 46 and seals the blister 46 within the interlock 55 in each wash position 36, 36 and reaction position 38. The lower peripheral seal 54B sealingly engages the waste pads 30, 30 and/or waste pad supports 42, 42 in each of the sample position 34 and wash positions 36, 36, and sealingly engages the microfluidic chip 64 and/or chip carrier 66 in the reaction position 38. The construction and characteristics of the lower peripheral seal 54B may be the same as or substantially similar the construction and characteristics of the upper peripheral seal 54A, as described above. In the illustrated embodiment, each peripheral seal 54A, 54B is a rubber gasket. However, as may be recognized by those of ordinary skill in the pertinent art based on the teachings herein, the seals may take any of numerous different configurations and may made of any of numerous different materials, and the device any include any desired number of seals, that are currently known or that later become known. In addition, rather than mount the upper and lower seals on the membrane support, they could be mounted on the other components of the device that engage the membrane support, such as the actuator/blister assemblies, the waste pads, the waste pad supports, the microfluidic chip and/or the chip carrier.

An exemplary operation of the device 10 includes the following procedural steps:

1) A biological sample 80 of about 100 µl to about 460 µl is collected in the sample receptacle 16. Samples can be saliva, urine, blood, or a swab in a buffered solution.
2) The sample receptacle cap 22 is closed and sealed causing the biological sample 80 to mix with a cell lysis solution 78. The cell lysis solution 78 may be any of numerous different lysis buffers that are currently known, or that later become known for performing this function, including detergent, salt solutions, chaotropic agents, or hypertonic solutions.
3) The sample receptacle 16 is inserted in the test cartridge 14 and the substantially complete contents 82 of the sample receptacle 16 are dispensed from the receptacle 16 into the test cartridge 14 using the manually operated pump 24 in the closure or cap 22 of the receptacle.
4) When the sample mixture 82 is dispensed into the test cartridge 14, it passes across the solid-state membrane 28 which adsorbs nucleic acids from the sample 80 as the solution 82 passes across the membrane and into the waste pad 30 contained in the test cartridge 14. The solid-state membrane 28 is then moved, in succession, to two wash positions 36, 36 where wash solutions are used to purify the captured nucleic acids.
5) The solid-state membrane 28 is then moved to a final reaction position 38 where a hypotonic solution is used to elute the captured nucleic acids adsorbed to the membrane 28. The solution and nucleic acids flow into the microfluidic reaction chambers 68, 68. The elution volume is in the range of about 15 µl to about 100 µl.
6) The movement of the elution solution into the reaction chambers 68, 68 hydrolyzes reagents stored dry in the reaction chambers.
7) The device 10 is then heated to a pre-determined temperature using a general or customized external heating device (not shown) in the base station 14. The temperature may be optimized for any number of isothermal amplification chemistries.
8) The amplified target (or the lack thereof) is determined by the amplified target nucleic acid binding to or interacting with colorimetric or fluorescent dyes.
9) The resulting color change or lack thereof allows the user to determine the presence of absence of the target in the original sample 80.

Figure 9:
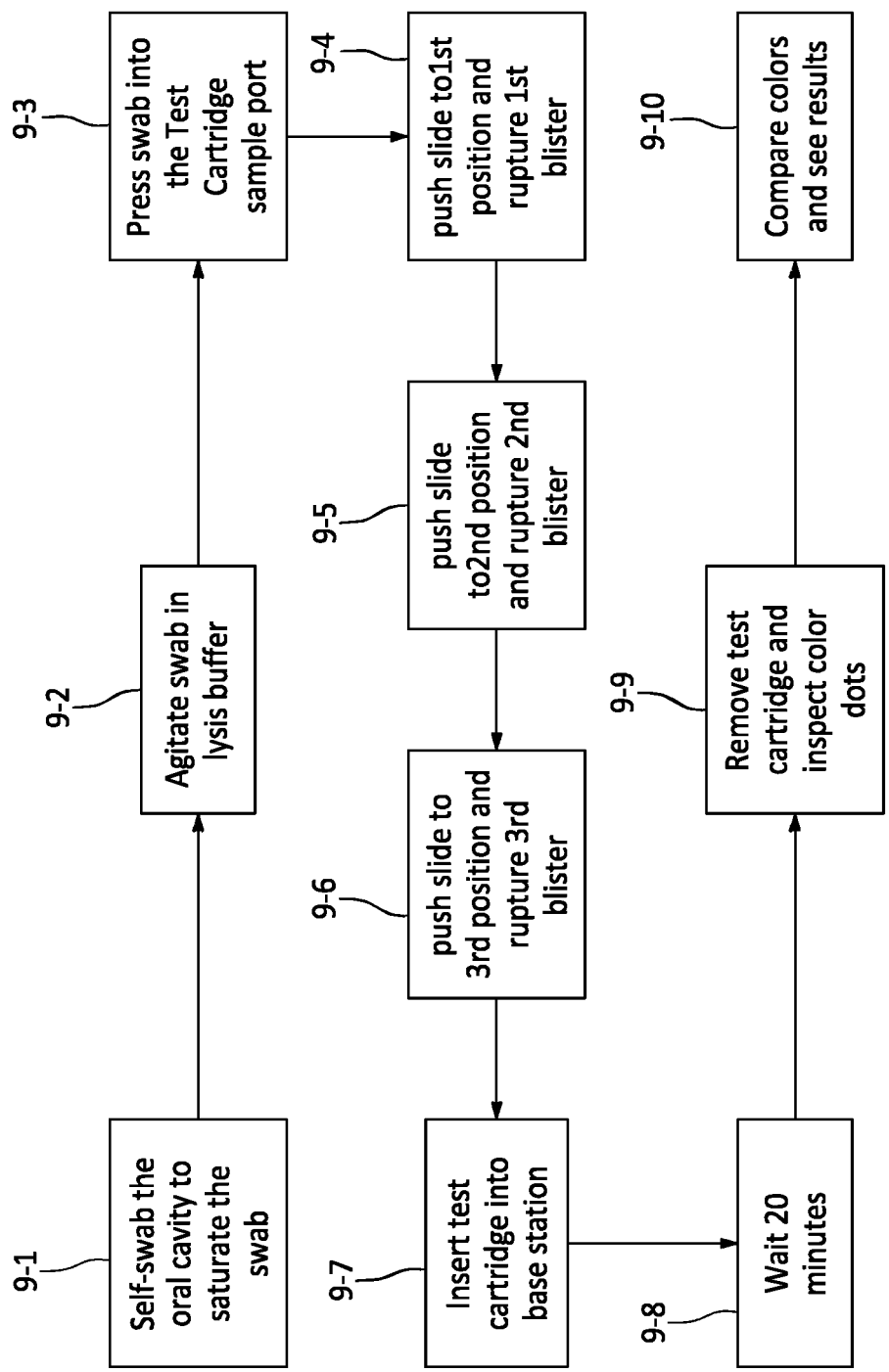
FIG. 9 is a flow chart illustrating a clinical workflow when performing a test, such as a test for Covid-19, with the device of FIGS. 1 and 2.

In FIG. 9, an exemplary clinical workflow for collecting and assaying a biological sample 80 with the device 10 is illustrated in further detail. First, in step 9-1, a sample 80 is collected using a cotton swab or equivalent device inserted into the mouth of the test subject and rubbed against surfaces containing saliva thereon. In step 9-2, once the swab is sufficiently saturated, the swab is agitated in the lysis buffer 78 of the vial 16 to break down cellular walls in the sample and release the nucleic acids contained therein. Next, in step 9-3, the swab is placed into the sample port 18 of the test cartridge 12 and onto the solid-state membrane 28 positioned in the sample position 34 to transfer the lysed sample 82 onto the solid-state membrane 28. In step 9-4, the knob 40 of the membrane slider 32 is manipulated to move the membrane slider 32 into a first wash position 36 and move the membrane 28 into a first wash station 44. Then, also in step 9-4, with the locking member 58 of the first actuator 48 moved to the unlocked position 62, the first actuator or plunger 48 is manually depressed, releasing the wash solution from the blister 46 at the first wash station to wash the solid-state membrane 28 at the first wash position 36. Next, in step 9-5, the slider knob 40 of the membrane slider 32 is used to push the membrane slider into the second wash position 36 and move the membrane 28 into the second wash station 44. Then, also in step 9-5, with the locking member 58 of the second plunger 48 moved to its unlocked position 62, the second plunger 48 is depressed, releasing the wash solution from the second blister 46 to wash the solid-state membrane 32 at the second wash position 36. In step 9-6, the slider knob 40 is then used to push the membrane slider 32 into the reaction position 38 and accordingly move the membrane 28 into the reaction station 69. Then, also in step 9-6, with the locking member 58 of a third plunger 48 moved to its unlocked position 62, the third plunger 48 is depressed, breaking the blister 46 and releasing its elution buffer onto the solid-state membrane 28 to elute the sample nucleic acids at the reaction position 36 into the microfluidic reaction chambers 66, 66 by capillary action. Then, in step 9-7, the test cartridge 12 is inserted into the base station 14, activating the heating element in the base station to provide the appropriate temperature for the amplification reaction. In step 9-8, the reaction chamber is heated a set period of time, e.g., about 20 minutes, for a LAMP amplification reaction. Then, in step 9-9, the test cartridge may be removed from the base station, and the results of the test are visible through the results window 70. In step 9-10, if the color of the sample indicator 76 matches the color of the negative control 72, the test indicates a negative result. If the color of the sample indicator 76 matches the color of the positive control 74, the test indicates a positive result.

Table 1 below includes in the first column the step number, in the second column the procedural steps for assaying a biological sample with the device of FIGS. 1 and 2, in the third column the primary function(s) performed at each such step, and in the fourth column variable(s) to be controlled at each such step.

TABLE 1

| Step No. | Assay Step | Primary Function(s) | Variables to be Controlled |
|---|---|---|---|
| 1 | Sample Collection | Collect saliva sample from patient Absorb saliva sample | 0.1 ml +− 0.02 ml |
| 2 | Sample preparation (use kit) | Chaotropic agent to lysis RNA/DNA from cell nucleus Dilute sample to target viscosity | 0.6 ml lysis chemistry + 0.1 sample = 0.7 ml total Time for diffusion of sample into diluent Time for chaotropic |

TABLE 1-continued

| Step No. | Assay Step | Primary Function(s) | Variables to be Controlled |
|---|---|---|---|
| | | | chemistry to complete Perform medium agitation (20 sec) |
| 3 | Position membrane and slider at sample load location | Exposes membrane to open sample port in this position as received | |
| 4 | Insert sample preparation vial into test cartridge port and depress pump | Dispense sample into sample port Flow sample onto membrane surface and through membrane bulk Absorb into waste pad | 0.7 ml lysed saliva Whatman FTA ® membrane size/volume Absorbent foam in contact with back side of membrane Foam capillarity Other "glass" membranes may be equivalent |
| 5 | Move slider to first blister location | Locate membrane under first blister | Force/Human Factors Detent to hold membrane in place Absorbent foam in contact with back side of membrane Foam capillarity |
| 6 | Actuate first blister (first wash buffer) by compressing first button | Wash sample on membrane surface (wash away cell pieces/parts and other unbound matter) Absorb into waste pad | Qiagen AW1 buffer 0.5 ml in blister Volume dispensed in sample membrane and positive control membrane |
| 7 | Move slider to second blister location | Locate membrane under second blister | Force/Human Factors Detent to hold membrane in place Absorbent foam in contact with back side of membrane Foam capillarity |
| 8 | Actuate second blister by depressing second button | Wash sample on membrane surface (wash away cell pieces and parts and other unbound matter) Absorb into waste pad | Qiagen AW2 buffer 0.5 ml Volume dispensed in sample membrane and positive control membrane |
| 9 | Optionally move slider to a membrane drying location (this operation is not present in the illustrated embodiments) | Dry membrane | Force/Human Factors Wait predetermined period of time |
| 10 | Move slider to third blister location | Locate membrane under third blister Engage and seal with microfluidics chip | Force/Human Factors Seal leakage requirement |
| 11 | Actuate third blister | Dispense elution buffer above reaction chamber Dispense molecular water into internal control and COVID test reaction chambers to mix with dried LAMP reagents Dispense molecular water into negative control reaction chambers to mix with dried LAMP reagents | Molecular H2O 0.06 ml through membrane and into chip 0.03 ml into negative control channel of chip Dispense volume per channel (all three channels positive, negative and sample) Channel must be filled - maximum predetermined percentage of air Rehydrolization of dried reagents |
| 12 | Plug inlet and outlet ports | Seal ports to prevent evaporation and/or DNA/RNA escaping into environment Baseline is paraffin washer seal on inlet port and hydro-plugging membrane on exit port | Seal leak rate Leak test negative pressure level |

As set forth in Table 1, first the biological sample 80 is collected and placed in the sample vial 16. The sample 80 is agitated with the lysis buffer 78 in the vial to break down cellular walls and release nucleic acids contained therein. Next, the sample receptacle 16 is placed into the sample port 18 of the test cartridge 14 and the pump 24 is depressed one or more times, to extrude the sample-lysis mixture 82 through the sample port 18 and across the solid-state membrane 28 positioned in the sample position 34. The slider knob 40 is then pushed forward to move the membrane slider 32 into the first wash position 36 and accordingly move the membrane 28 into the first wash station 44. The first actuator or plunger 48 is then depressed, releasing the wash solution from the sealed chamber or blister 46 to wash the sample or captured nucleic acids at the first wash position 36. Next, the slider knob 40 is pushed to move the membrane slider 32 into the second wash position 36 and accordingly move the membrane 28 into the second wash station 44. The second actuator or plunger 48 is then depressed, releasing the wash solution from the sealed chamber or blister 46 to wash the sample or captured nucleic acids at the second wash position 36. Following the second wash, the solid-state membrane is allowed to dry. If desired, the slider knob 40 may be manipulated to move the membrane slider 32 into a drying position. For example, the drying position may be located between the second wash position 36 and the reaction position 38. Next, the slider knob 40 is pushed to move the membrane slider 32 into the reaction position 38 and accordingly move the membrane 28 into the reaction station 69. Then, with the locking member 58 of the third actuator or plunger 48 moved to the unlocked position 62, the third actuator or plunger 48 is depressed, releasing the elution buffer from the sealed chamber or blister 46 to elute the sample nucleic acids at the reaction position into the microfluidic chip 64. Finally, the test cartridge 12 is inserted into the base station 14 to begin nucleic acid amplification. When the test cartridge 12 is inserted, inlet and outlet ports of the reaction chambers may be closed by paraffin seals. The heating element (not shown) in the base station provides the appropriate temperature for the LAMP reaction, which as shown in the illustrated embodiment, is about 63° C. If necessary, this temperature is sufficient to melt paraffin seals and open respective inlet and/or outlet ports. During this step, after a set period of time, e.g., about 28 minutes, the results of the test will be visible through the results window 70. The results window 70 contains the negative control 72, the positive control 74, and the sample indicator 76. If the color of the sample indicator 76 matches color of the negative control 72, the test indicates a negative result. If the color of the sample indicator 76 matches the color of the positive control 74, the test indicates a positive result.

Turning to FIGS. 14A and 14B, another embodiment of a device including a disposable cartridge that is received within a base station for amplifying and detecting nucleic acids in a biological sample is indicated generally by the reference number 110. The device 110 of FIGS. 14A-14B differs from the cartridge described above in that it is a true microfluidic "Lab On Chip Device." The device 110 of FIGS. 14A-14B does not require a moving membrane slider, waste pad or chip components. Rather, it is a passive-monolithic device that contains each assay function. As can be seen, the device 110 is a smart fluidic channel design, where blister activation sequence and passive valving control each of the assay operations as needed. Inherently, the fluid channel when activated in proper sequence will purge residual fluid from the solid-state membrane with a small burst of air before each sequential step, without an extra supply of air. Toxic lysing buffer is safely contained in a blister and is isolated from the user. As shown in FIG. 15, an off-the-shelf absorbent sample collection device 112 (Super-SAL) works with the integrated syringe body style sample port 114 of the device 110.

Figure 16:
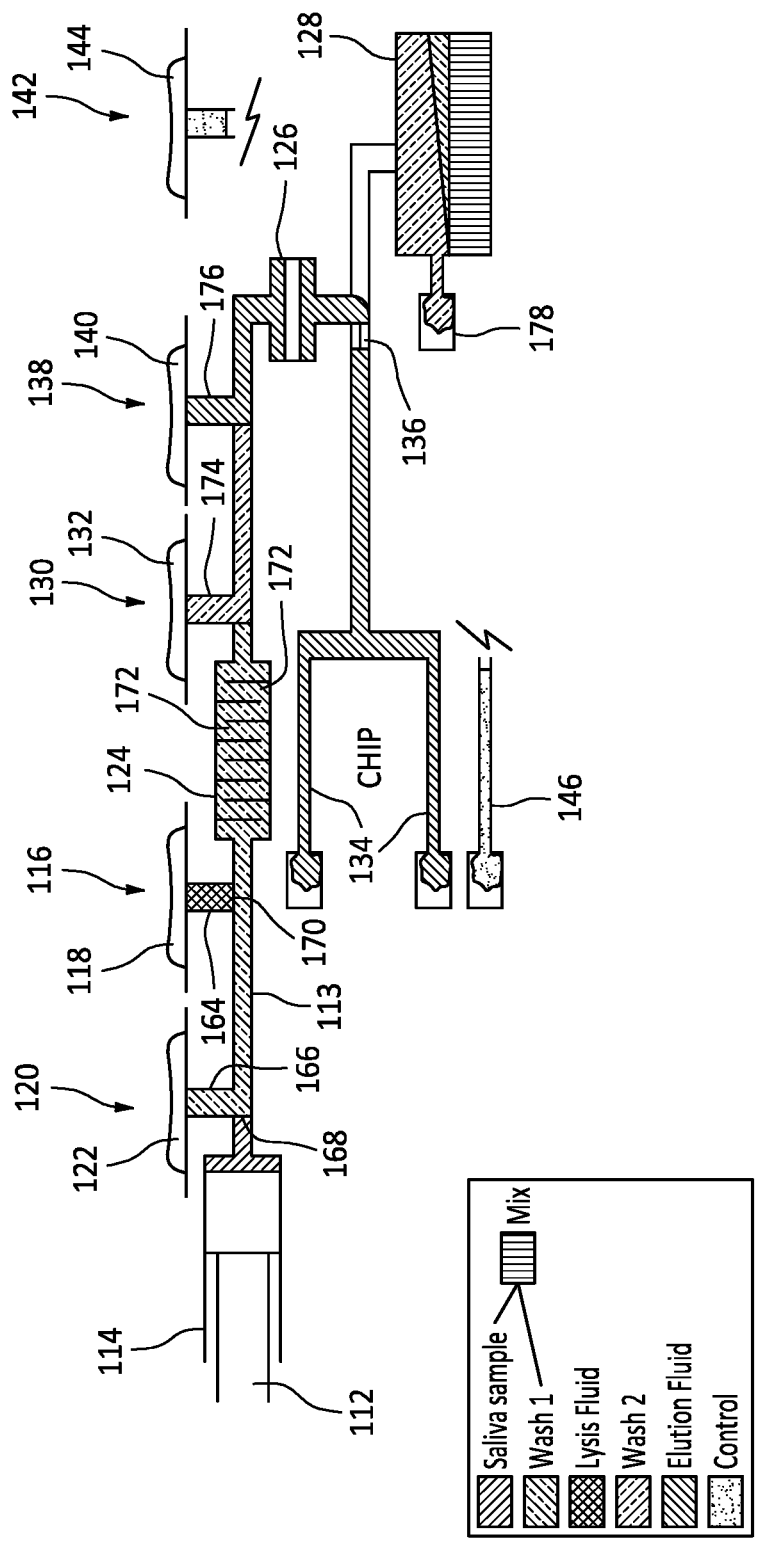
FIG. 16 is a somewhat schematic illustration of the device of FIGS. 14A and 14B illustrating the introduction of a saliva sample through a sample port, where the device includes a first wash station, a lysis station, a mixing chamber, a second wash station, an elution station, a solid-state membrane, a waste chamber and microfluidic reaction chambers, wherein the lysis and wash solutions are received within the waste chamber which, in turn, creates a sufficient back pressure to open a one-way valve between the solid-state membrane and the microfluidic reaction chambers to allow the elution fluid and targeted nucleic acids to flow through the one-way valve and into the microfluidic reaction chambers.

As shown in FIG. 16, a saliva or other biological sample is inserted into a sample port 114, such as via the sample collection device 112, where the liquid sample enters a microfluidic conduit 113 of the microfluidic device 110. The sample collection device 112 includes a saliva collection swab 109 for collecting saliva thereon and a syringe-type plunger 111 for compressing the saliva collection swab 109 within the sample port 114 to release the saliva therefrom and into the microfluidic conduit 113. A lysis station 116 including a lysis buffer blister 118, and a first wash station 120 including a wash buffer blister 122, are then depressed simultaneously. As shown in FIG. 16, this pushes the sample solution and the lysis buffer from the lysis blister 118 into a static mixer 124 for mixing the sample and lysis buffer. As shown in FIG. 16, the sample-lysis mixture then passes through a solid-state, RNA/DNA capture membrane 126 and into a waste container 128 built into the device 110. At this point, the target RNA or DNA is captured on the solid-state membrane 126. The membrane 126 is then washed with the first wash solution from the first wash blister 122 of the first wash station 120, which also passes through the membrane 126 and into the waste container 128. The first wash solution from the first wash blister 122 and the sample/lysis mixture are separated by an air pocket generated when the first wash blister 122 is depressed. A second wash station 130 including a second wash blister 132 is then depressed and the second solution passes through the solid-state membrane 126 and into the waste container 128. The first and second wash solutions are also separated by an air pocket. At this point, the waste container 128 is full and creates a back pressure that diverts the subsequent fluids, i.e., the eluent(s), into the reaction chambers 134, 134 through a one-way valve 136 in fluid communication between the solid-state membrane 126 and the reaction chambers 134, 134. An eluent station 138 including an eluent blister 140 is then depressed to, in turn, cause the eluent to pass from the eluent blister 140 through the membrane 126, and release the captured RNA or DNA into the corresponding reaction chambers 134, 134. In the illustrated embodiment, the device 110 includes two reaction chambers 134, 134; however, as may be recognized by those of ordinary skill in the pertinent art based on the teaching herein, the device may include any desired number of reaction chambers, including from about one to about five reaction chambers, or any other number of chambers. In a separate fluidic path, a negative control station 142 including a negative control blister 144 is depressed to release a negative control fluid and fill the negative control chamber 146. As may be recognized by those of ordinary skill in the pertinent art based on the teachings herein, the device 110, or the base station for receiving the device 110, may include an actuator or plunger associated with each blister that may be the same as or similar to those set forth above and that may be manually or otherwise engageable to depress and rupture the blisters and, in turn, release their fluids in the desired sequence as set forth herein.

Figure 17B:
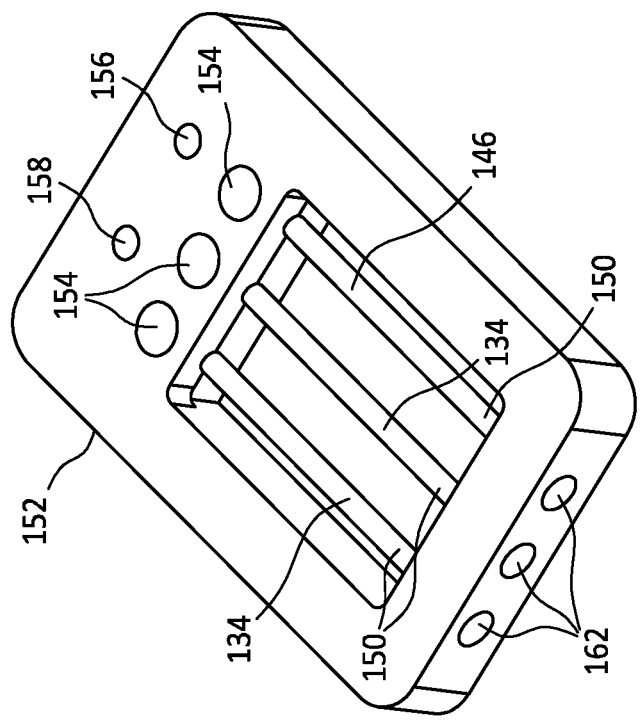
FIGS. 17A and 17B are perspective views of the capillary tube LAMP reaction chip of the device of FIGS. 14A and 14B where the microfluidic reaction chip includes three reaction chambers.
Figure 17A:
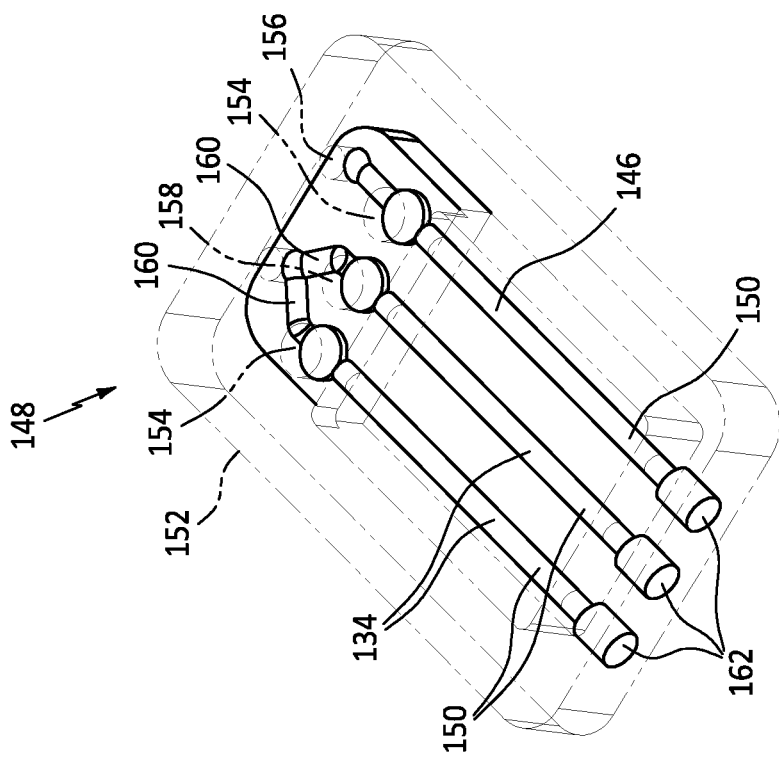

Turning to FIGS. 17A and 17B, the capillary tube LAMP reaction chip 148 included within the device 110 of FIGS. 14A-14B is illustrated. LAMP reaction lab assay kits are sensitive to thermal gradients, material interactions and incomplete filling of the reaction chamber(s). Glass capillary tubes have excellent thermal conductivity, are chemically inert, and have capillary fill properties making the structure perform better than other options when used in a LAMP reaction device.

The capillary tube LAMP reaction chip 148 illustrated in FIG. 17A-17B utilizes three glass capillary tubes 150 that are over-molded or co-molded into a polymer resin chassis 152 that, as can be seen, integrates the capillary tubes, molded fluid channels and features for ancillary components. The integrated design allows for simultaneous filling of the internal control chamber and CV-19 or other reaction chambers 134, 134 with elutant, while the negative control 146 is filled from an isolated blister 144, as shown in FIGS. 14A-14B and described above.

Included in each of the three channels 150, 150 is a unique reconstitution chamber 154, 154 where stabilized master-mix reagents are placed during assembly. In FIG. 17B, each reconstitution chamber 154, 154 is shown capped or sealed to retain the master-mix reagents, such as lyophilized master mix pellets, therein. The chassis 152 defines a negative control inlet 156 in fluid communication between the negative control station 142 (FIG. 16) and the negative control reaction chamber 146, and a another inlet 158 in fluid communication between the solid state membrane 126 (FIG. 16) and the internal control reaction chamber 134 and the CV-19 or other reaction chamber 134. As shown in FIG. 17A, the chassis 152 defines a split fluid path 160 between the inlet 158 and the two reconstitution chambers 154, 154 for the reaction chambers 134, 134. When in use, during elution, each of the reconstitution chambers 154, 154 fills and simultaneously reconstitutes each master mix lyosphere into a homogeneous mixture that is delivered directly into the reaction chambers 134, 134 and 146 fully mixed and ready for the LAMP reaction. As shown in FIGS. 17A and 17B, a vent 162, 162 is located within the chassis 152 at the downstream end of each reaction chamber 134, 134 and 146 and is in fluid communication with the respective reaction chamber. Each vent 162 is filled or plugged with a material that allows air or other gas to vent therethrough as each tube 150, 150 is filled with eluent, but that does not allow liquid to pass therethrough, such as a hydrophobic vent membrane, in order to retain the eluent and reaction components within each respective chamber.

More generally, glass provides for alternative embodiments outside of capillary tubes. For example, laminated glass structure assemblies could be employed as well. These embodiments use planar (like a microscope slide) glass elements in a laminated structure where internal microfluidic channels are fabricated through common glass fabrication and bonding processes. These structures could also be glass and polymer composite assemblies.

Figure 18:
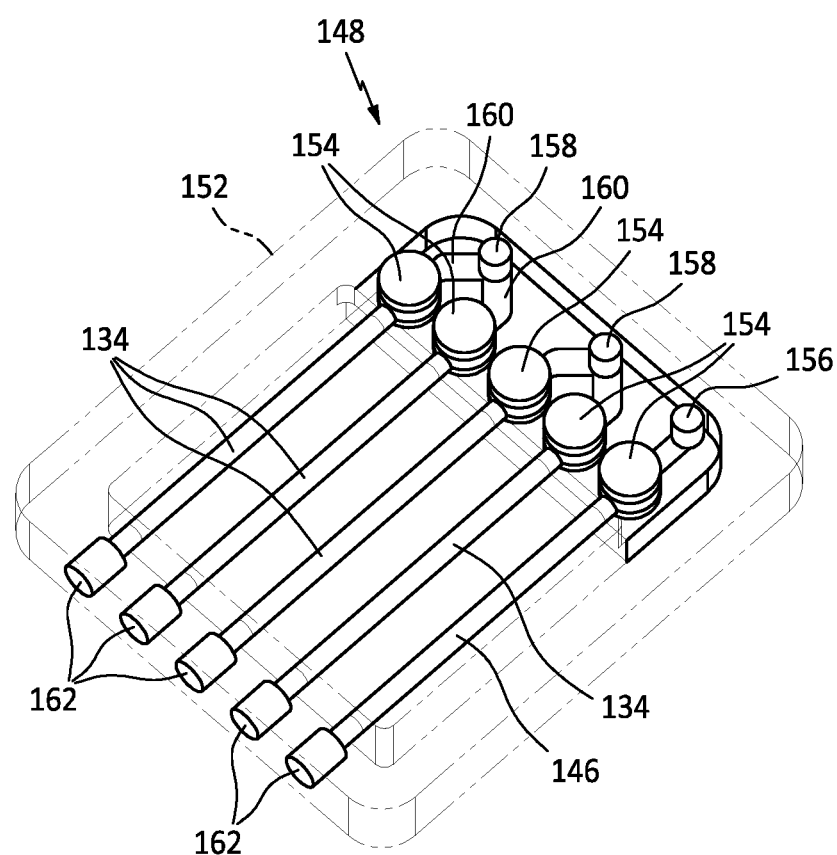
FIG. 18 is a perspective view of an alternative embodiment of a capillary tube LAMP reaction chip of the device of FIGS. 14A and 14B where the microfluidic reaction chip includes five reaction chambers.

In FIG. 18, another capillary tube LAMP reaction chip 148 that may be mounted within the device 110 of FIGS. 14A-14B includes five reaction chambers rather than the three reaction chambers as shown in the device of FIGS. 17A-17B above. As can be see, the LAMP reaction chip of FIG. 18 includes one negative control reaction chamber 146 and four reaction chambers 134, 134. In the illustrated embodiment, each pair of reaction chambers 134, 134 includes an internal control reaction chamber and a CV-19 or other reaction chamber. As may be recognized by those of ordinary skill in the pertinent art based on the teachings herein, any desired number of glass capillary reaction tube chambers may be employed. One advantage of the glass reaction tubes is that they can both improve the reaction and, as can been seen, allow visualization of the colored test results therethrough.

As shown in FIG. 16, the device 110 further comprises a lysis leg 164 extending in fluid communication between the lysis station 116 and the sample conduit 113 and configured to direct the flow of the lysis agent from the lysis station/blister into the sample conduit 113. A first wash leg 166 extends in fluid communication between the first wash station 120 and the sample conduit 113 at a point upstream relative to the lysis leg 164 and is configured to direct the flow of the first wash solution from the first wash station/blister into the sample conduit 113 behind the sample-lysis mixture. As can be seen, the first wash leg 166 is in fluid communication with the sample conduit 113 at a sample-wash junction 168 located adjacent to the sample port 114 and configured to allow a substantial portion of the sample to flow into the sample conduit 113 downstream of the sample-wash junction 168 prior to introducing the first wash solution through the first wash leg 166 and into the sample conduit 113. The lysis leg 164 is in fluid communication with the sample conduit 113 at a sample-lysis junction 170 located downstream of the sample-wash junction 168 and is configured to allow the lysis agent to mix with the sample and form the sample-lysis mixture and the first wash solution to flow into the sample conduit behind or upstream of the sample-lysis mixture.

As shown in FIG. 16, the static mixer 124 is in fluid communication between the sample-lysis junction 170 and the solid-state membrane 126 to mix the sample and lysis agent and form a sample-lysis mixture prior to passage across the solid-state membrane 126. As indicated schematically in FIG. 16, in the exemplary embodiment, the static mixer 124 defines a plurality of axially-spaced recesses or grooves 172, 172 formed in the sample conduit to facilitate mixing the sample and lysis therein. However, as may be recognized by those of ordinary skill in the pertinent art based on the teachings herein, the mixer may take the form of any of numerous different mixers, including static mixers, that are currently known, or that later become known, such as, for example, pulsatile flow mixers, rotational flow mixers, and combinatorial micromixers.

As shown in FIG. 16, the second wash station 130 is configured to introduce the second wash solution into the sample conduit 113 following the first wash solution and to pass the second wash solution across the solid-state membrane 126 to purify nucleic acids captured therein. The second wash solution passes across the solid-state membrane 126 and is received in the waste chamber 128. A second wash leg 174 is in fluid communication between the second wash station 130 and the sample conduit 113 downstream of the first wash leg 166 and is configured to direct the flow of the second wash solution from the second wash station/blister into the sample conduit 113. The second wash solution is released from the chamber of the second wash blister 132 through the second wash leg 174 and into the sample conduit 113, is passed across the solid-state membrane 126 to purify nucleic acids captured therein, and is received in the waste chamber 128.

The elution station 138 includes the elution blister 140 defining a sealed eluent chamber containing the eluent. An elution leg 176 extends in fluid communication between the elution station 138 and the solid-state membrane 126. Upon depressing the elution blister 140, the eluent is released from the chamber of the elution blister 140 through the elution leg 176 and across the solid-state membrane 126 to elute captured nucleic acids from the solid-state membrane and pass the captured nucleic acids into the reaction chambers 134, 134.

As shown in FIG. 16, the waste chamber 128 includes a waste chamber vent 178 in fluid communication between the waste chamber and ambient atmosphere. The waste chamber vent 178 defines an open condition and a closed condition. In the open condition fluid passing across the solid-state membrane 126 is received within the waste chamber 128. In the closed condition fluid passing across the solid-state member 126 is prevented from passing into the waste chamber 128. During passage of the sample-lysis mixture and first and second wash solutions across the solid-state membrane 126, the waste chamber vent 178 is in the open condition and the sample-lysis mixture and the wash solutions passing across the solid-state membrane flow into the waste chamber 128 and are prevented from flowing into the reaction chambers 134, 134. As may be recognized by those of ordinary skill in the pertinent art based on the teachings herein, the waste chamber vent may take any of numerous different configurations that are currently known, or that later become known, for performing the function of the waste chamber vent as described herein. For example, the waste chamber vent may include a valve movable between open and closed positions, or could include a hydrophobic membrane, in order to create sufficient back pressure to direct the flow of eluent across the solid-state membrane 126 through the reaction chamber valve 136 and into the reaction chambers 134, 134.

As shown in FIG. 16, the reaction chamber valve 136 (i) is closed to prevent fluid flow into the reaction chambers 134, 134 when the fluid pressure between the solid-state membrane 126 and the reaction chamber valve 136 is below a valve-opening pressure, and (ii) is open to allow fluid flow into the reaction chambers 134, 134 when the fluid pressure between the solid-state membrane 126 and the reaction chamber valve 136 is above the valve-opening pressure. In the illustrated embodiment, closure of the waste chamber vent 178 causes the fluid pressure between the solid-state membrane 126 and reaction chamber valve 136 to exceed the valve-opening pressure and thereby allow fluid flow from the solid-state membrane 126 into the reaction chambers 134, 134 and not into the waste chamber 128.

As indicated above, the sequence of fluid activation/release from the blisters will purge residual fluid from the solid-state membrane 126 with a small burst of air before each sequential step. In the illustrated embodiment, the bursts of air are provided by the legs 164, 166, 174 and 176 extending between each respective station and the sample conduit 113 and/or solid state membrane 126. In other words, each such leg is filled with air such that when the respective blister is depressed and the fluid is released through the respective leg, the air in the leg forms an air gap separating the fluid on either side of the air gap. These pockets or bursts of air also pass over the solid-state membrane and can facilitate drying or evaporating chemical constituents from the membrane, if desired.

As may be recognized by those of ordinary skill in the pertinent art based on the teachings herein, numerous changes, improvements, modifications, additions and deletions may be made to the above-described and other embodiments of the present invention without departing from the scope of the invention. For example, the components of the device may take any of numerous different configurations and may be made of any of numerous materials that are currently known or later become known, and features may be added to or removed therefrom, without departing the from the scope of the invention. Accordingly, this detailed description of embodiments is to be taken in an illustrative as opposed to a limiting sense.

What is claimed is:

1. A device comprising:
    a sample port for receiving therein a biological sample;
    a lysis chamber including a lysis agent therein;
    a mixing chamber for mixing the biological sample and lysis agent into a sample-lysis mixture;
    a wash station including a wash solution therein;
    an elution station including an eluent therein;
    a solid-state membrane located downstream of the mixing chamber, wash station and elution station, and configured to capture nucleic acids in the biological sample passed across the membrane;
    a waste chamber located downstream of the solid-state membrane; and
    a reaction chamber located downstream of the solid-state membrane;
    wherein the sample port, lysis chamber and mixing chamber are configured to mix the biological sample and lysis agent to form a sample-lysis mixture, pass the sample-lysis mixture across the solid-state membrane to capture nucleic acids in the biological sample therein, and receive any remainder of the sample-lysis mixture in the waste chamber, the wash station is configured to introduce the wash solution across the solid-state membrane to purify nucleic acids captured therein, and receive the wash solution from the solid-state membrane in the waste chamber, and the elution station is configured to pass the eluent across the solid-state membrane, elute captured nucleic acids from the solid-state membrane, and pass the captured nucleic acids into the reaction chamber for amplifying the captured nucleic acids, and
    further comprising a sample conduit in fluid communication between each of the sample port, the lysis chamber and the wash station, and the solid-state membrane, wherein the sample conduit includes the mixing chamber therein, the sample port, lysis chamber and sample conduit are configured to mix the sample and lysis agent to form the sample-lysis mixture, pass the sample-lysis mixture across the solid-state membrane to capture nucleic acids in the biological sample therein, and receive any remainder of the sample-lysis mixture in the waste chamber, the wash station is configured to introduce the wash solution into the sample conduit following the sample-lysis mixture, pass the wash solution across the solid-state membrane to purify nucleic acids captured therein, and receive the wash solution from the solid-state membrane in the waste chamber, and the elution station is configured to pass the eluent across the solid-state membrane, elute captured nucleic acids from the solid-state membrane, and pass the captured nucleic acids into the reaction chamber for amplifying the captured nucleic acids, and
    (i) a lysis leg extending in fluid communication between the lysis chamber and the sample conduit and configured to direct a flow of the lysis agent from the lysis chamber into the sample conduit, and (ii) a wash leg extending in fluid communication between the wash station and the sample conduit at a point upstream relative to the lysis leg and configured to direct a flow of the wash solution from the wash station into the sample conduit behind the sample-lysis mixture.

2. A device as defined in claim 1, wherein the mixing chamber is defined by a static mixer within the sample conduit in fluid communication between a sample-lysis junction and the solid-state membrane to mix the sample and lysis agent and form the sample-lysis mixture prior to passage across the solid-state membrane.

3. A device as defined in claim 1, further comprising a lyophilized reconstitution chamber in fluid communication between the solid-state membrane and the reaction chamber, wherein the elution station is configured to pass the eluent across the solid-state membrane, elute captured nucleic acids from the solid-state membrane, pass the captured nucleic acids through the lyophilized agent reconstitution chamber and reaction chamber for amplifying the captured nucleic acids.

4. A device as defined in claim 1, wherein (i) the wash leg is in fluid communication with the sample conduit at a sample-wash junction located adjacent to the sample port and configured to allow a substantial portion of the sample to flow into the sample conduit downstream of the sample-wash junction prior to introducing the wash solution through the wash leg and into the sample conduit; and (ii) the lysis leg is in fluid communication with the sample conduit at a sample-lysis junction located downstream of the biological sample-wash junction and configured to allow the lysis agent to mix with the sample and form the sample-lysis mixture and the wash solution to flow into the sample conduit behind or upstream of the sample-lysis mixture.

5. A device as defined in claim 4, further comprising a second wash station in fluid communication with the sample conduit and including a second wash solution therein, wherein the second wash station is configured to introduce the second wash solution into the sample conduit following the other wash solution and to pass the second wash solution across the solid-state membrane to purify nucleic acids captured therein, and wherein the second wash solution passed across the solid-state membrane is receivable in the waste chamber.

6. A device as defined in claim 5, wherein the second wash station includes a sealed wash chamber containing the second wash solution, a second wash leg extending in fluid communication between the second wash station and the sample conduit downstream of the other wash leg and configured to direct a flow of the second wash solution from the second wash station, through the second wash leg, into the sample conduit, and across the solid-state membrane to purify nucleic acids captured therein, and wherein the second wash solution is receivable in the waste chamber.

7. A device as defined in claim 1, wherein the elution station includes a sealed eluent chamber containing the eluent, an elution leg extending in fluid communication between the elution station and the solid-state membrane, wherein the eluent chamber is configured to release the eluent from the eluent chamber through the elution leg and across the solid-state membrane to elute captured nucleic acids from the solid-state membrane and pass the captured nucleic acids into the reaction chamber.

8. A device as defined in claim 1, further comprising a waste chamber vent in fluid communication between the waste chamber and ambient atmosphere, wherein the waste chamber vent defines an open condition and a closed condition, configured such that in the open condition fluid that passes across the solid-state membrane is received within the waste chamber, and in the closed condition fluid that passes across the solid-state member is prevented from passing into the waste chamber.

9. A device as defined in claim 8, configured such that during passage of the sample-lysis mixture and wash solution across the solid-state membrane, the waste chamber vent is in the open condition and the sample-lysis mixture and the wash solution that passes across the solid-state membrane flows into the waste chamber and are prevented from flowing into the reaction chamber.

10. A device as defined in claim 9, further comprising a waste vent seal movable between an open position allowing fluid to flow out of the waste chamber vent and thereby allow fluid to flow into the waste chamber, and a closed position sealing the waste chamber vent and thereby preventing fluid from flowing into the waste chamber.

11. A device as defined in claim 10, further comprising a reaction chamber valve in fluid communication between the solid-state membrane and the reaction chamber, wherein the reaction chamber valve configured to be (i) closed to prevent fluid flow into the reaction chamber when a fluid pressure between the solid-state membrane and the reaction chamber valve is below a valve-opening pressure and (ii) open to allow fluid flow into the reaction chamber when the fluid pressure between the solid-state membrane and the reaction chamber valve is above the valve-opening pressure.

12. A device as defined in claim 11, wherein movement of the waste vent seal into the closed position causes the fluid pressure between the solid-state membrane and reaction chamber valve to exceed the valve-opening pressure and thereby allow fluid flow from the solid-state membrane into the reaction chamber.

13. A device as defined in claim 1, further comprising a saliva collection swab for collecting saliva thereon and receivable within the sample port for introducing the saliva directly into the sample port and sample conduit for mixture with the lysis agent.

14. A device as defined in claim 1, further comprising a body, wherein at least one of the solid-state membrane or the body is movable relative to the other from (i) a sample position where the solid-state membrane is in fluid communication with the sample port for receiving across the solid-state membrane the biological sample and capturing nucleic acids in the biological sample therein, (ii) to a wash position where the solid-state membrane is in fluid communication with the wash station for passage of the wash solution across the solid-state membrane to purify nucleic acids captured therein, and (iii) to a reaction position where the solid-state membrane is in fluid communication with the reaction chamber for eluting captured nucleic acids from the solid-state membrane into the reaction chamber and amplifying captured nucleic acids.

15. A device comprising:
a sample port for receiving therein a biological sample;
a lysis chamber including a lysis agent therein;
a mixing chamber for mixing the biological sample and lysis agent into a sample-lysis mixture;
a wash station including a wash solution therein;
an elution station including an eluent therein;
a solid-state membrane located downstream of the mixing chamber, wash station and elution station, and configured to capture nucleic acids in the biological sample passed across the membrane;
a waste chamber located downstream of the solid-state membrane; and
a reaction chamber located downstream of the solid-state membrane;
wherein the sample port, lysis chamber and mixing chamber are configured to mix the biological sample and lysis agent to form a sample-lysis mixture, pass the sample-lysis mixture across the solid-state membrane to capture nucleic acids in the biological sample therein, and receive any remainder of the sample-lysis mixture in the waste chamber, the wash station is configured to introduce the wash solution across the solid-state membrane to purify nucleic acids captured therein, and receive the wash solution from the solid-state membrane in the waste chamber, and the elution station is configured to pass the eluent across the solid-state membrane, elute captured nucleic acids from the solid-state membrane, and pass the captured nucleic acids into the reaction chamber for amplifying the captured nucleic acids, and
further comprising a body, wherein at least one of the solid-state membrane or the body is movable relative to the other from (i) a sample position where the solid-state membrane is in fluid communication with the sample port for receiving across the solid-state membrane the biological sample and capturing nucleic acids in the biological sample therein, (ii) to a wash position where the solid-state membrane is in fluid communication with the wash station for passage of the wash solution across the solid-state membrane to purify nucleic acids captured therein, and (iii) to a reaction position where the solid-state membrane is in fluid communication with the reaction chamber for eluting captured nucleic acids from the solid-state membrane into the reaction chamber and amplifying captured nucleic acids, and wherein the wash station defines a plurality of wash stations, wherein at least one of the solid-state membrane or the body is movable relative to the other from the sample position to a plurality of successive wash positions, and in each wash position, the solid-state membrane is in fluid communication with a respective one of the plurality of wash stations for passage of respective wash solution across the solid-state membrane to purify nucleic acids captured therein.

16. A device as defined in claim 14, wherein the body further includes an absorbent waste pad in fluid communication with the waste chamber and engageable with the solid-state membrane in the sample position for absorbing therein fluid passed through the solid-state membrane in the sample position and/or engageable with the solid-state membrane in the wash position for absorbing therein the wash solution passed through the solid-state membrane in the wash position.

17. A device as defined in claim 16, further comprising a waste pad support movably mounted on the body and including the waste pad mounted thereon, and wherein the waste pad is movably engageable with an underside of the solid-state membrane for engagement of the solid-state membrane and waste pad.

18. A device as defined in claim 15, further comprising a membrane support including the solid-state membrane mounted thereon, a microfluidic chip defining the reaction chamber as a microfluidic reaction chamber, and a microfluidic chip support movably mounted on the body and including the microfluidic chip mounted thereon, wherein the microfluidic chip is engageable with at least one of the solid-state membrane or membrane support upon movement of the solid-state membrane into the reaction position to for fluid communication between the solid-state membrane and the microfluidic reaction chamber.

19. A device as defined in claim 14, further comprising a membrane support including the solid-state membrane mounted thereon, wherein at least one of the membrane support or body is movable relative to the other from the sample position to the wash position, and from the wash position to the reaction position, and the membrane support includes a manually-engageable portion that is manually engageable to move the membrane support and membrane thereon from the sample position to the wash position, and from the wash position to the reaction position.

20. A device as defined in claim 1, wherein at least one of the wash station or elution station includes a sealed chamber respectively containing a wash solution or eluent, and an actuator movable between a non-actuated position and an actuated position, wherein in the actuated position the respective wash solution or eluent is released from the chamber.

21. A device as defined in claim 20, wherein the actuator is manually engageable and moveable from the non-actuated position to the actuated position, and the sealed chamber includes a frangible or breakable wall that is breakable by the actuator in the actuated position to release the wash solution or eluent from the sealed chamber.

22. A device as defined in claim 21, wherein the manually-engageable actuator is a plunger and the sealed chamber is defined by a blister containing the respective wash solution or eluent therein, and movement of the plunger from the non-actuated to the actuated position causes the plunger to break the blister and release the respective wash solution or eluent.

23. A device comprising:
a sample port for receiving therein a biological sample;
a lysis chamber including a lysis agent therein;
a mixing chamber for mixing the biological sample and lysis agent into a sample-lysis mixture;
a wash station including a wash solution therein;
an elution station including an eluent therein;
a solid-state membrane located downstream of the mixing chamber, wash station and elution station, and configured to capture nucleic acids in the biological sample passed across the membrane;
a waste chamber located downstream of the solid-state membrane; and
a reaction chamber located downstream of the solid-state membrane;
wherein the sample port, lysis chamber and mixing chamber are configured to mix the biological sample and lysis agent to form a sample-lysis mixture, pass the sample-lysis mixture across the solid-state membrane to capture nucleic acids in the biological sample therein, and receive any remainder of the sample-lysis mixture in the waste chamber, the wash station is configured to introduce the wash solution across the solid-state membrane to purify nucleic acids captured therein, and receive the wash solution from the solid-state membrane in the waste chamber, and the elution station is configured to pass the eluent across the solid-state membrane, elute captured nucleic acids from the solid-state membrane, and pass the captured nucleic acids into the reaction chamber for amplifying the captured nucleic acids, and
further comprising a body, wherein at least one of the solid-state membrane or the body is movable relative to the other from (i) a sample position where the solid-state membrane is in fluid communication with the sample port for receiving across the solid-state membrane the biological sample and capturing nucleic acids in the biological sample therein, (ii) to a wash position where the solid-state membrane is in fluid communication with the wash station for passage of the wash solution across the solid-state membrane to purify nucleic acids captured therein, and (iii) to a reaction position where the solid-state membrane is in fluid communication with the reaction chamber for eluting captured nucleic acids from the solid-state membrane into the reaction chamber and amplifying captured nucleic acids,
wherein at least one of the wash station or elution station includes a sealed chamber respectively containing a wash solution or eluent, and an actuator movable between a non-actuated position and an actuated position, wherein in the actuated position the respective wash solution or eluent is released from the chamber, and further comprising a membrane support including the solid-state membrane mounted thereon, wherein at least one of the membrane support or body is movable relative to the other from the sample position to the wash position, and from the wash position to the reaction position, and wherein the actuator includes a locking member movable between a locked position preventing actuation of the actuator, and an unlocked position allowing the actuator to be moved from the non-actuated position to the actuated position, and the locking member is engageable with the membrane support upon relative movement into the wash position or reaction position to move the locking member from the locked position to the unlocked position.

24. A device as defined in claim 23, wherein the locking member is pivotally or rotatably mounted on the body and engageable with the membrane support, and upon movement of the membrane support into the wash positon or reaction position, the membrane support causes the locking member to rotate from the locked position to the unlocked position.

25. A device as defined in claim 1, further comprising (i) a disposable cartridge containing the sample port, wash station, elution station, solid-state membrane, waste chamber and reaction chamber, and (ii) a base station configured to receive the disposable cartridge therein and including a heat source for providing heat for a reaction in the reaction chamber.

26. A device comprising:
a sample port for receiving therein a biological sample;
a lysis chamber including a lysis agent therein;
a mixing chamber for mixing the biological sample and lysis agent into a sample-lysis mixture;
a wash station including a wash solution therein;
an elution station including an eluent therein;
a solid-state membrane located downstream of the mixing chamber, wash station and elution station, and configured to capture nucleic acids in the biological sample passed across the membrane;
a waste chamber located downstream of the solid-state membrane; and
a reaction chamber located downstream of the solid-state membrane;
wherein the sample port, lysis chamber and mixing chamber are configured to mix the biological sample and lysis agent to form a sample-lysis mixture, pass the sample-lysis mixture across the solid-state membrane to capture nucleic acids in the biological sample therein, and receive any remainder of the sample-lysis mixture in the waste chamber, the wash station is configured to introduce the wash solution across the solid-state membrane to purify nucleic acids captured therein, and receive the wash solution from the solid-state membrane in the waste chamber, and the elution station is configured to pass the eluent across the solid-state membrane, elute captured nucleic acids from the solid-state membrane, and pass the captured nucleic acids into the reaction chamber for amplifying the captured nucleic acids; and
further comprising a sample receptacle including therein the lysis chamber and the mixing chamber and configured to receive therein the biological sample for mixture with the lysis agent, and an outlet port connectable in fluid communication with the sample port for releasing the lysis agent and biological sample mixture into the sample port and onto the solid-state membrane, and the sample receptacle includes a sealed chamber containing the lysis agent, and a frangible or breakable wall configured to be ruptured after receiving the biological sample therein to allow mixture of the lysis agent and biological sample.

27. A device as defined in claim 26, wherein the sample receptacle includes a closure movable between an open position for allowing introduction of the biological sample into the sample receptacle, and a closed position sealing the biological sample and lysis agent within the receptacle, at least one protuberance engageable with the frangible or breakable wall when the closure is in the closed position to break the frangible or breakable wall and thereby mix the lysis agent with the biological sample, and a pump that is manually engageable to pump the lysis agent and biological sample mixture through the outlet port and into the sample port.

28. A method of capturing nucleic acids in a biological sample and amplifying the captured nucleic acids therein in a reaction chamber, the method comprising the following steps:
(i) receiving a biological sample in a device, wherein the device comprises a sample port for receiving therein the biological sample;
a lysis chamber including a lysis agent therein;
a mixing chamber for mixing the biological sample and lysis agent into a sample-lysis mixture;
a wash station including a wash solution therein;
an elution station including an eluent therein;
a solid-state membrane located downstream of the mixing chamber, wash station and elution station, and configured to capture nucleic acids in the biological sample passed across the membrane;
a waste chamber located downstream of the solid-state membrane; and
a reaction chamber located downstream of the solid-state membrane;
wherein the sample port, lysis chamber and mixing chamber are configured to mix the sample and lysis agent to form a sample-lysis mixture, pass the sample-lysis mixture across the solid-state membrane to capture nucleic acids in the biological sample therein, and receive the remainder of the sample-lysis mixture in the waste chamber, the wash station is configured to introduce the wash solution across the solid-state membrane to purify nucleic acids captured therein, and receive the wash solution from the solid-state membrane in the waste chamber, and the elution station is configured to pass the eluent across the solid-state membrane, elute captured nucleic acids from the solid-state membrane, and pass the captured nucleic acids into the reaction chamber for amplifying the captured nucleic acids, and
further comprising a sample conduit in fluid communication between each of the sample port, the lysis chamber and the wash station, and the solid-state membrane, wherein the sample conduit includes the mixing chamber therein, the sample port, lysis chamber and sample conduit are configured to mix the sample and lysis agent to form the sample-lysis mixture, pass the sample-lysis mixture across the solid-state membrane to capture nucleic acids in the biological sample therein, and receive any remainder of the sample-lysis mixture in the waste chamber, the wash station is configured to introduce the wash solution into the sample conduit following the sample-lysis mixture, pass the wash solution across the solid-state membrane to purify nucleic acids captured therein, and receive the wash solution from the solid-state membrane in the waste chamber, and the elution station is configured to pass the eluent across the solid-state membrane, elute captured nucleic acids from the solid-state membrane, and pass the captured nucleic acids into the reaction chamber for amplifying the captured nucleic acids, and
(a) a lysis leg extending in fluid communication between the lysis chamber and the sample conduit and configured to direct a flow of the lysis agent from the lysis chamber into the sample conduit, and (b) a wash leg extending in fluid communication between the wash station and the sample conduit at a point upstream relative to the lysis leg and configured to direct a flow of the wash solution from the wash station into the sample conduit behind the sample-lysis mixture;
(ii) passing the biological sample and sample-lysis mixture across solid-state membrane and capturing nucleic acids in the biological sample in the solid-state membrane;
(iii) preventing the flow of the sample-lysis mixture that passes across the solid-state membrane into the reaction chamber, and receiving the remainder of the sample-lysis mixture that passes across the solid-state membrane in the waste chamber;
(iv) passing the wash solution across the solid-state membrane and purifying nucleic acids captured therein;
(v) preventing the flow of the wash solution that passes across the solid-state membrane into the reaction chamber, and receiving the remainder of wash solution that passes across the solid-state membrane in the waste chamber; and
(vi) passing the eluent across the solid-state membrane and eluting captured nucleic acids from the solid-state membrane, directing the eluted captured nucleic acids from the solid-state membrane into the reaction chamber and not into the waste chamber, and amplifying captured nucleic acids therein in the reaction chamber.

29. A method as defined in claim 28, wherein step (i) includes introducing the lysis agent into a sample conduit, mixing the lysis agent with the biological sample to form the sample-lysis mixture, passing the sample-lysis mixture across the solid-state membrane and capturing nucleic acids in the biological sample therein; steps (iii) and (iv) include introducing the wash solution into the sample conduit following the sample-lysis mixture, passing the wash solution across the solid-state membrane and purifying nucleic acids captured from the sample-lysis mixture therein, preventing the flow of the wash solution into the reaction chamber, and receiving the wash solution that passes through the solid-state membrane in the waste chamber; and step (v) includes introducing the eluent across the solid-state membrane and eluting captured nucleic acids from the solid-state membrane, substantially preventing the captured nucleic acids from flowing into the waste chamber, directing the captured nucleic acids into the reaction chamber, and amplifying the captured nucleic acids in the reaction chamber.

30. A method as defined in claim 29, further comprising closing a vent to the waste chamber after receiving the lysis agent and wash solution therein, and opening an inlet valve to the reaction chamber for directing the captured nucleic acids from the solid-state membrane therein.

31. A method as defined in claim 28, wherein step (iii) includes moving at least one of the solid-state membrane or the wash station relative to the other into a first wash position, step (v) includes moving at least one of the solid-state membrane or the reaction chamber relative to the other into a reaction position and eluting captured nucleic acids from the solid-state membrane into the reaction chamber and amplifying captured nucleic acids therein.

32. A method as defined in claim 28, wherein the reaction chamber defines a microfluidic reaction chamber, the method further comprising moving at least one of the solid-state membrane or a support for the solid-state membrane into a reaction position, and upon moving the solid-state membrane or support therefor into the reaction position, moving a microfluidic chip containing the microfluidic reaction chamber into engagement with an underside of at least one of the solid-state membrane or the support therefor and placing the microfluidic reaction chamber in fluid communication with the solid-state membrane.

33. A method as defined in claim 28, further comprising introducing a cartridge containing the biological sample and lysis agent, solid-state membrane, wash solution, eluent and reaction chamber into a base station, performing at least step (v) with the cartridge located in the base station, and disposing of the cartridge after use.

34. A method as defined in claim 28, wherein (i) the wash leg is in fluid communication with the sample conduit at a sample-wash junction located adjacent to the sample port and configured to allow a substantial portion of the sample to flow into the sample conduit downstream of the sample-wash junction prior to introducing the wash solution through the wash leg and into the sample conduit; and (ii) the lysis leg is in fluid communication with the sample conduit at a sample-lysis junction located downstream of the biological sample-wash junction and configured to allow the lysis agent to mix with the sample and form the sample-lysis mixture and the wash solution to flow into the sample conduit behind or upstream of the sample-lysis mixture.

35. A method as defined in claim 34, wherein the device further comprises a second wash station in fluid communication with the sample conduit and including a second wash solution therein, wherein the second wash station is configured to introduce the second wash solution into the sample conduit following the other wash solution and to pass the second wash solution across the solid-state membrane to purify nucleic acids captured therein, and wherein the second wash solution passed across the solid-state membrane is receivable in the waste chamber.

36. A method as defined in claim 35, wherein the second wash station includes a sealed wash chamber containing the second wash solution, a second wash leg extending in fluid communication between the second wash station and the sample conduit downstream of the other wash leg and configured to direct a flow of the second wash solution from the second wash station, through the second wash leg, into the sample conduit, and across the solid-state membrane to purify nucleic acids captured therein, and wherein the second wash solution is receivable in the waste chamber.

* * * * *